(12) United States Patent
Fukuma et al.

(10) Patent No.: US 7,341,349 B2
(45) Date of Patent: Mar. 11, 2008

(54) OPHTHALMOLOGIC APPARATUS AND OPHTHALMOLOGIC CHART

(75) Inventors: Yasufumi Fukuma, Tokyo (JP); Kohji Nishio, Tokyo (JP); Takefumi Hayashi, Tokyo (JP); Eiichi Yanagi, Tokyo (JP); Noriyuki Nagai, Tokyo (JP); Yasuo Kato, Tokyo (JP); Yukio Ikezawa, Tokyo (JP); Mineki Hayafuji, Tokyo (JP); Tadashi Okamoto, Tokyo (JP); Masakazu Hayashi, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 616 days.

(21) Appl. No.: 10/495,467

(22) PCT Filed: Nov. 15, 2002

(86) PCT No.: PCT/JP02/11942

§ 371 (c)(1),
(2), (4) Date: May 13, 2004

(87) PCT Pub. No.: WO03/041572

PCT Pub. Date: May 22, 2003

(65) Prior Publication Data

US 2005/0012896 A1 Jan. 20, 2005

(30) Foreign Application Priority Data

Nov. 15, 2001 (JP) ............................. 2001-350705

(51) Int. Cl.
*A61B 3/02* (2006.01)
(52) U.S. Cl. ..................................... 351/240; 351/237
(58) Field of Classification Search ........ 359/237–243; 345/22, 23, 25, 156
See application file for complete search history.

(56) References Cited

U.S. PATENT DOCUMENTS

| | | | | |
|---|---|---|---|---|
| 4,753,527 A | * | 6/1988 | Ishihara | 351/244 |
| 5,231,430 A | * | 7/1993 | Kohayakawa | 351/243 |
| 5,444,504 A | * | 8/1995 | Kobayashi et al. | 351/237 |
| 5,483,305 A | * | 1/1996 | Kohayakawa | 351/243 |
| 5,629,748 A | | 5/1997 | Hayashi et al. | 351/232 |
| 6,244,713 B1 | | 6/2001 | Hayashi | 351/237 |

FOREIGN PATENT DOCUMENTS

JP 3176669 B2 4/2001

* cited by examiner

*Primary Examiner*—M. Hasan
(74) *Attorney, Agent, or Firm*—Chapman and Cutler LLP

(57) ABSTRACT

An optometric apparatus 2 according to the present invention comprises a body portion 5r provided with an optical system for a right eye for projecting a chart for the right eye in order to inspect visual function of both eye of an examinee and a body portion 5l provided with an optical system for a left eye for projecting a chart for the left eye, the optical systems for the right and left eyes projecting the same fusion patterns to perform fusion of the both eyes of the examinee.

10 Claims, 21 Drawing Sheets

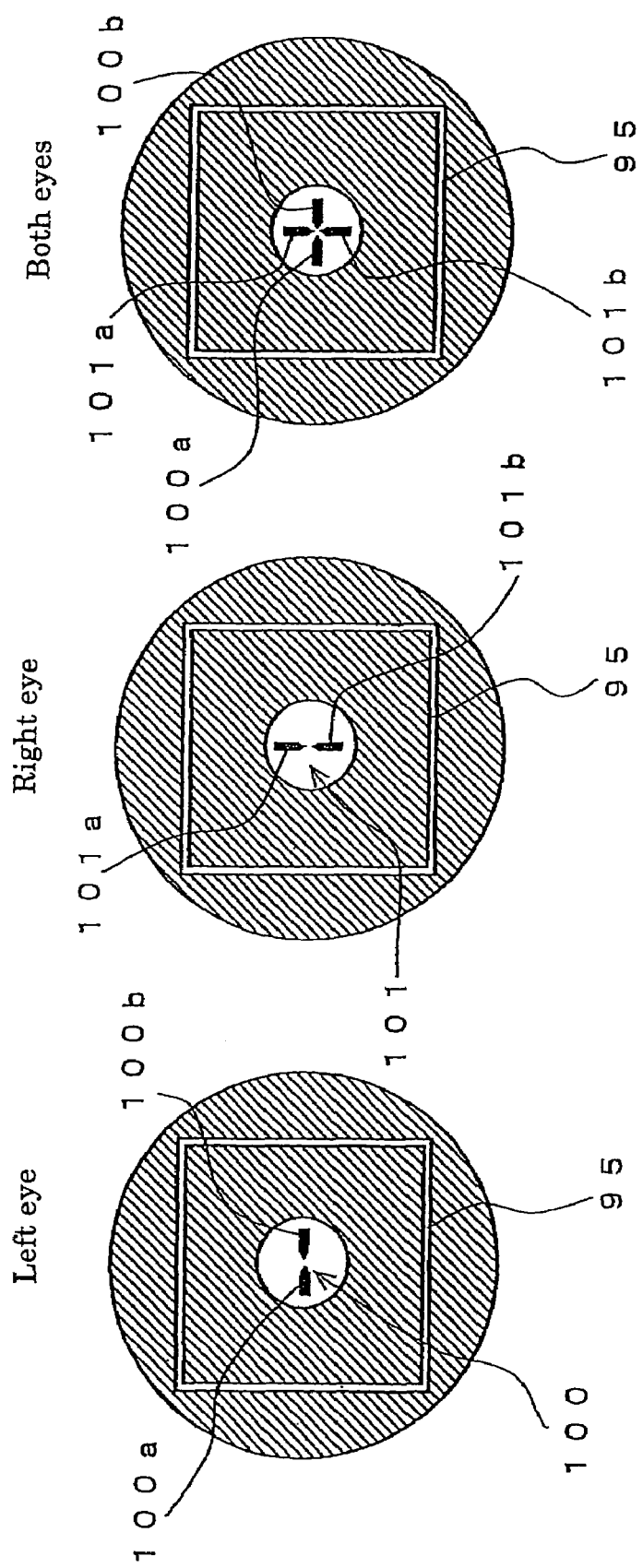

102r      102g

103

OPHTHALMOLOGIC APPARATUS AND OPHTHALMOLOGIC CHART

TECHNICAL FIELD

The present invention relates to an optometric apparatus including independently an optical system for a right eye for projecting a chart for the right eye and an optical system for a left eye for projecting a chart for the left eye, in order to inspect visual function of both eyes of an examinee and an optometric chart used in the optometric apparatus.

BACKGROUND ART

Conventionally there is known an optometric apparatus including independently an optical system for a right eye for projecting a chart for the right eye and an optical system for a left eye for projecting a chart for the left eye, in order to inspect visual function of both eyes of an examinee. For example, in a subjective device for inspecting vision or eyesight, if vision of the right eye of the examinee is measured, a chart of a Landolt ring or the like is projected by the optical system for the right eye, if the vision of the left eye is measured, a chart is projected by the optical system for the left eye and if visions of both eyes are measured, the same charts are projected by the optical systems for the right and left eyes.

By the way, accommodation and convergence are increased/decreased together in the daily life and appear to have an un-separable relation with each other, but actually the convergence is increased and decreased while maintaining constantly the accommodation or the accommodation can be changed to certain degree while maintaining the convergence constantly. For example, phenomenon for changing only the accommodation while doing a single distinct vision of a target means a relative accommodation, a scope between both extremes in which the single distinct vision is eventually impossible by increasing gradually a degree or power of a concave and convex wear lens means a relative accommodation region, and the fact shown in a degree or power of the lens means a relative accommodation power (area). Moreover, when wearing to the both eyes or one eye a prism whose base is disposed outward or inward, instead of a spherical lens, phenomenon of obtaining the single distinct vision by overcoming the prism means a relative convergence, the fact of showing this with a degree of convergence means a relative convergence power (width). However, even in a scope that the relative accommodation and the relative convergence are possible, there is a case comfortable to view with the both eyes, it is known that a relationship between the accommodation and the convergence at that time in a healthy people are positioned on the Donders convergence line (see Document 1). On the other hand, when looking an instrument such as a telescope or binoculars, there is appeared generally a phenomenon of an instrumental near sight in which visual accommodation is in a side of the near sight, while, it is known that the instrumental near sight represents a value of –0.5 D to –1 D based on a visual axial angle, a power of adjustment pursuant to the age, a size of visual field, brightness of the visual field, a state of refraction and so on in case of monops or single eye and binocle or both eyes and binocular observation, and the relationship between the accommodation and the convergence tends to separate from the Donders convergence line (see Document 2 as described hereinafter).

[Document 1]
Editor: Akira Ogiwara "Physiology of Eyes" Igaku-Shoin pp. 358-365, 1966

[Document 2]
Editors: Nin Ohotsuka, Shinichi Kano "Rinnshou Ganka Zensyo, No. 20 Vols." Eye Function III Kanahara Syuppan pp. 462-463, 1970

Accordingly, in the optometric apparatus as described above, if it is desired that the visual function of the both eyes is inspected on the assumption that the different charts are projected by the optical systems for the right and left eyes, and the charts are recognized as one chart with the both eyes, there is a case that the examinee occurs an adjustment by the instrumental near sight, the relationship between the accommodation and the convergence separates from the Donders convergence line and the projected charts of the optical systems for the right and left are viewed to the examinee into a rightward and leftward and unstable rocking condition. Otherwise, if the examiner has an oblique position which is no problem in the daily life, despite it is desired that the an inspection is proceeded without considering the oblique position, normally, the fusion of the projected charts of the optical systems for the right and left eyes are not performed due to the oblique position and as a result there is a problem that the charts are viewed to the examinee in a deviated condition.

Even though the same charts are projected by the optical systems for the right and left eyes, because the charts are one body substantially, the examinee does not have appreciation of seeing a near position when near point inspection for vision, for example, if the examinee has the oblique position there is a case that the both eyes are not converged and the fusion is not performed. Furthermore, even if the both eyes converge when performing the near point inspection for vision, if the relationship between the accommodation and the convergence separates from the Donders convergence line, there is a problem that the fusion of the projected charts of the optical systems for the right and left eyes is also not performed easily and the examinee often has a whole of a time for inspection, actually.

The present invention is made in view of the above circumstances and it is an object to provide an optometric apparatus in which projected charts of optical systems for right and left eyes are prevented from viewing in a deviated sate, and an optometric chart used for the optometric apparatus.

DISCLOSURE OF INVENTION

An optometric apparatus according to the present invention comprises an optical system for a right eye, for projecting a chart for the right eye and an optical system for a left eye, for projecting a chart for the left eye, in order to inspect visual function of both eyes of an examinee, and it is characterized in that the optical systems for the right and left eyes project the same fusion patterns in order to perform a fusion of the both eyes of the examinee.

The fusion pattern is preferably formed into a frame shape to surround the charts for the right and left eyes when the fusion pattern is projected simultaneously with the charts for the right and left eyes, and the fusion pattern may be projected by either of two colors being attached selectively.

The optical systems for the right and left eyes may project targets for inspecting oblique positions or targets for inspecting visions, as the charts for the right and left eyes, if the targets for inspecting the visions are projected, when a distance from eyes of the examinee to be examined to the targets for inspecting the visions is variable optically, a convergence angle determined by optical axes of the optical systems for the right and left eyes preferably varies pursuant to the distance.

In the optical systems for the right and left eyes, means for projecting the fusion patterns for the right and left eyes may be provided separately from or integrally with means for projecting charts for the left and left eyes, it may be decided based on design conditions space and cost, which structure is adopted. The charts for the right and left eyes can be projected by rotational target plates or liquid crystal displays and the fusion patterns may be also projected by rotational target plates or liquid crystal displays, further the fusion patterns may be used for distinction of a state in inspection of astigmatism (cross cylinder test).

BRIEF DESCRIPTION OF DRAWINGS

FIG. 16(a) is an explanatory view showing a chart for an oblique positional inspection, projected to the left eye, FIG. 16(b) is an explanatory view showing a chart for an oblique positional inspection, projected to the right eye, and FIG. 16(c) is an explanatory view showing a chart obtained by combination of the charts in Figs. (a) and (b).

BEST MODE FOR CARRYING OUT THE INVENTION

A mode for carrying out the present invention will be explained with reference to the drawings below.

Figure 1:
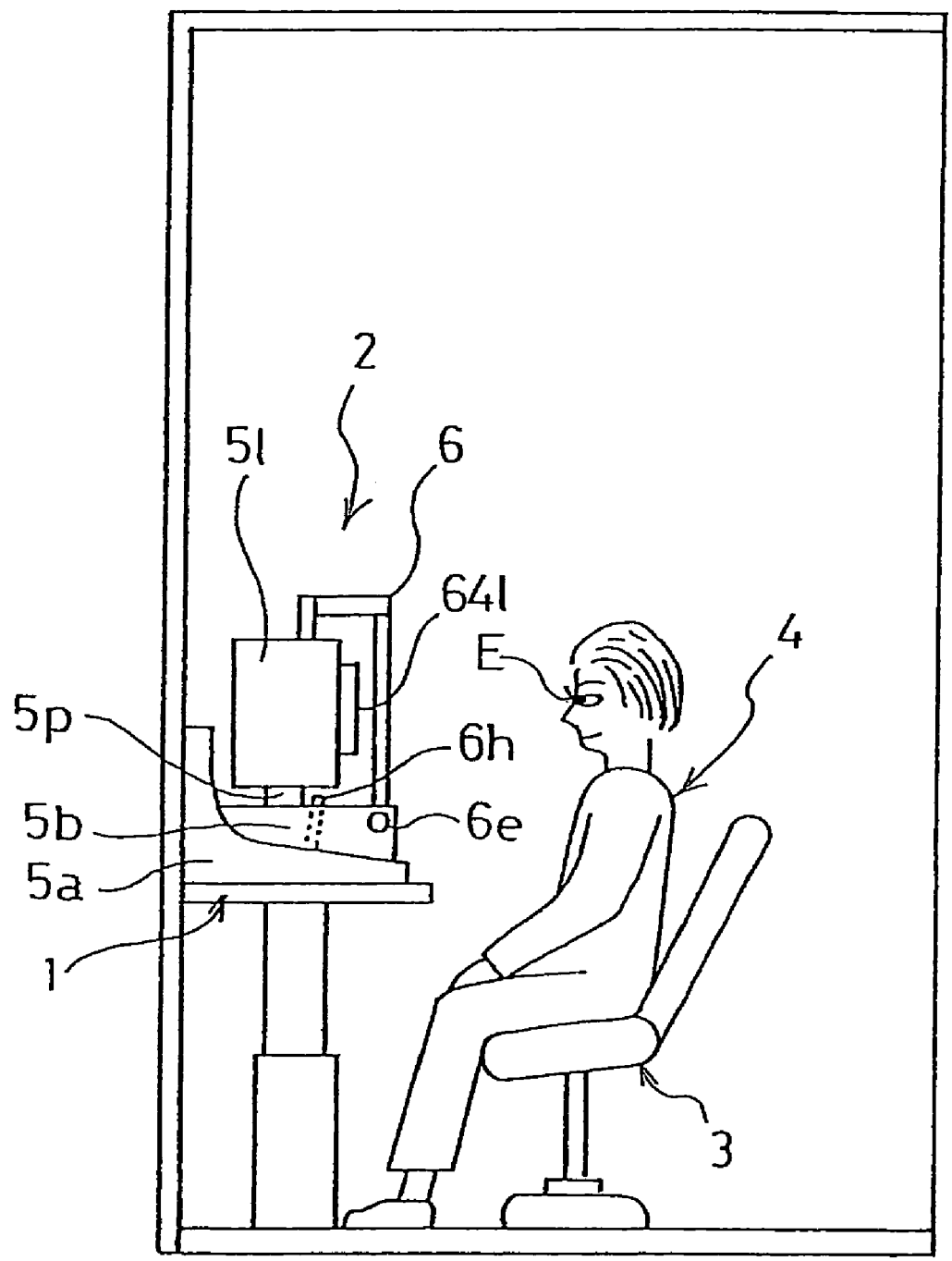
FIG. 1 is an explanatory view showing an example of installation of an optometric apparatus according to the present invention.
Figure 2:
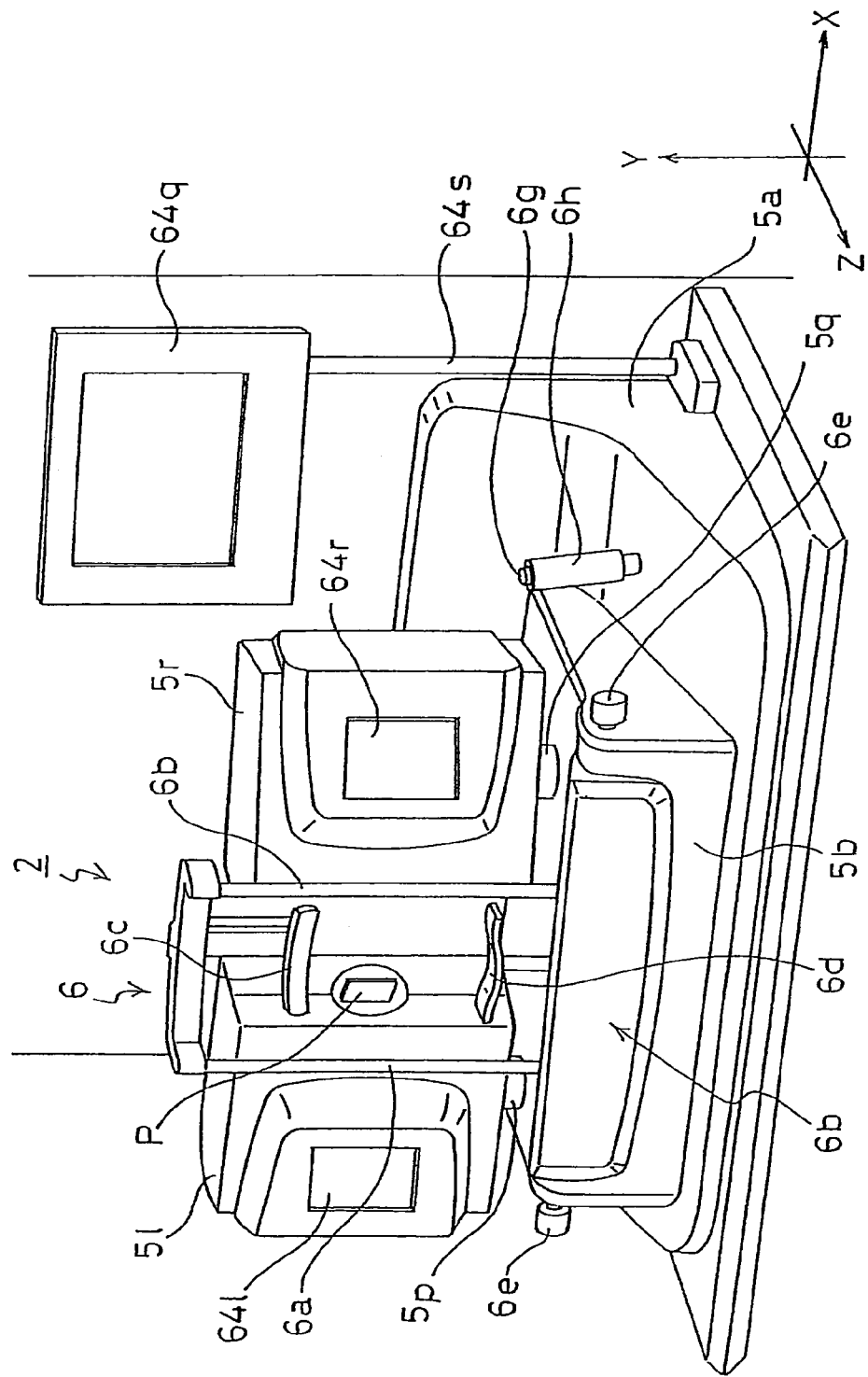
FIG. 2 is view showing an outline of the optometric apparatus shown in FIG. 1.

In FIG. 1, 1 is a table whose height can be adjusted upward and downward, 2 is an optometric apparatus disposed on the table 1, 3 is a chair disposed in front of the table 1, and 4 is an examinee seated on the chair 3. The optometric apparatus 2 has, as shown in FIG. 2, a base portion 5a, a box 5b for a driving mechanism, a pair of right-and-left body portions 5l and 5r, each containing therein a measurement optical system which will be mentioned later and a face receiving device 6. The body portions 5l and 5r are supported by supports 5p and 5q.

The face receiving device 6 is provided with a pair of supports 6a and 6b and a jaw receiver 6d. The pair of supports 6a and 6b is provided with an arc-state forehead receiver 6c, which has a circular arc shape as viewed from top plan. A position of the jaw receiver 6d can be adjusted in an upward and downward direction (a direction of Y) by knobs 6e and 6e. A position of the forehead receiver 6c can also be adjusted in a fore-and-aft direction.

Figure 10:
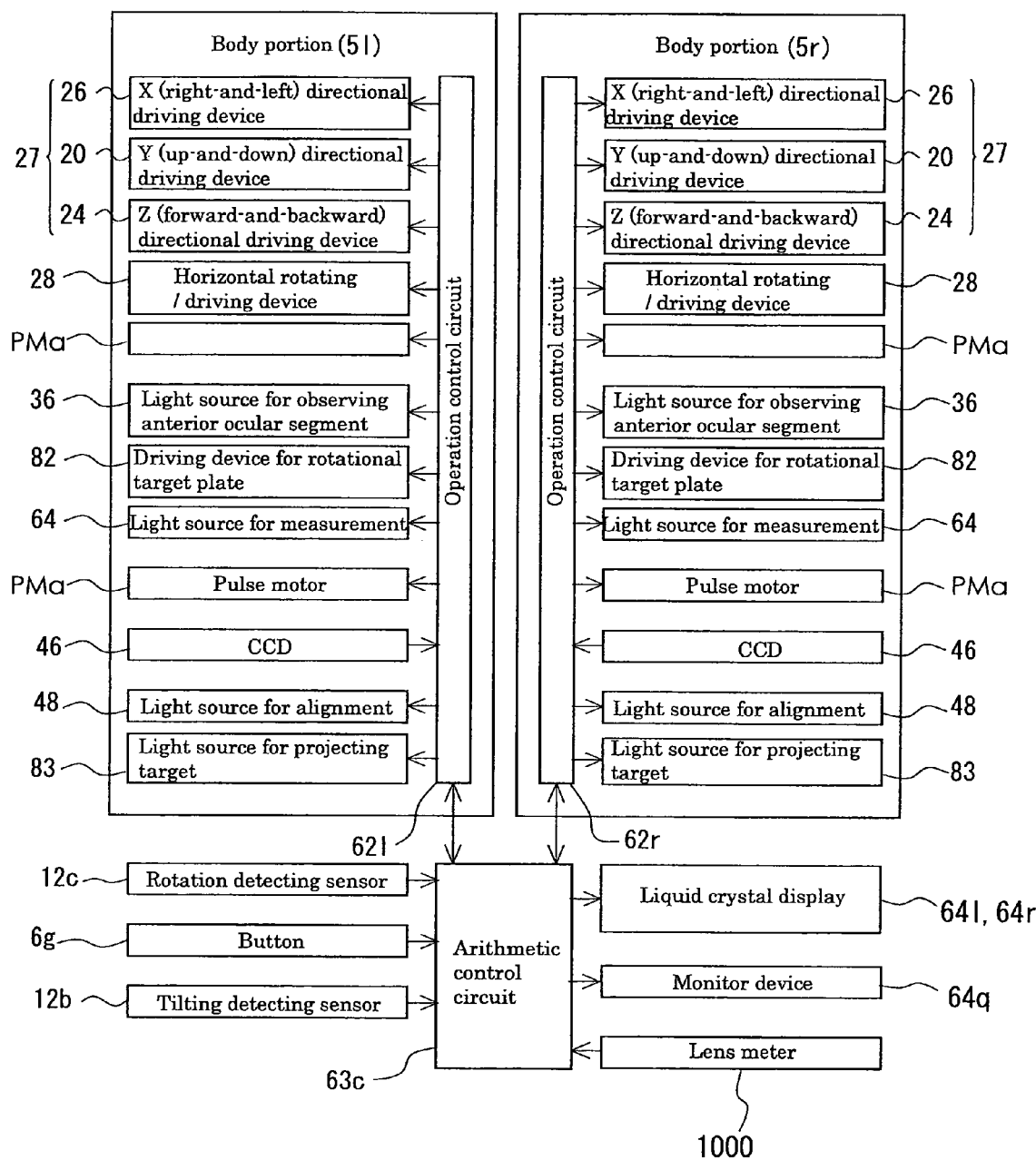
FIG. 10 is a block view showing a control system of the optometric apparatus in FIG. 1.

Within the driving mechanism box 5b is an XYZ driving mechanism 27 for independently driving the supports 5p and 5q in X, Y and Z directions, respectively, (see FIG. 10). The XYZ driving mechanism 27 is composed of an X directional driving device 26 for driving the support 5p or 5q in the X direction, a Y directional driving device 20 for driving the support 5p or 5q in the Y direction, and a Z directional driving device 24 for driving the support 5p or 5q in the Z direction. A known structure, in which for example, a pulse driving motor and a feeding screw are used, can be applied to each of the driving devices.

In the driving mechanism box 5b is a horizontal rotary driving device 28 for rotating and driving the supports 5p and 5q in a horizontal plane and in opposite directions with respect to each other. For this rotary driving mechanism, a combination of a pulse motor and a gear may be used. The base portion 5a is provided with a joystick lever (hereinafter referred to as a lever) 6h disposed in a position in which the examinee 4 is easy to operate. The lever 6h is provided with a button 6g.

Figure 3:
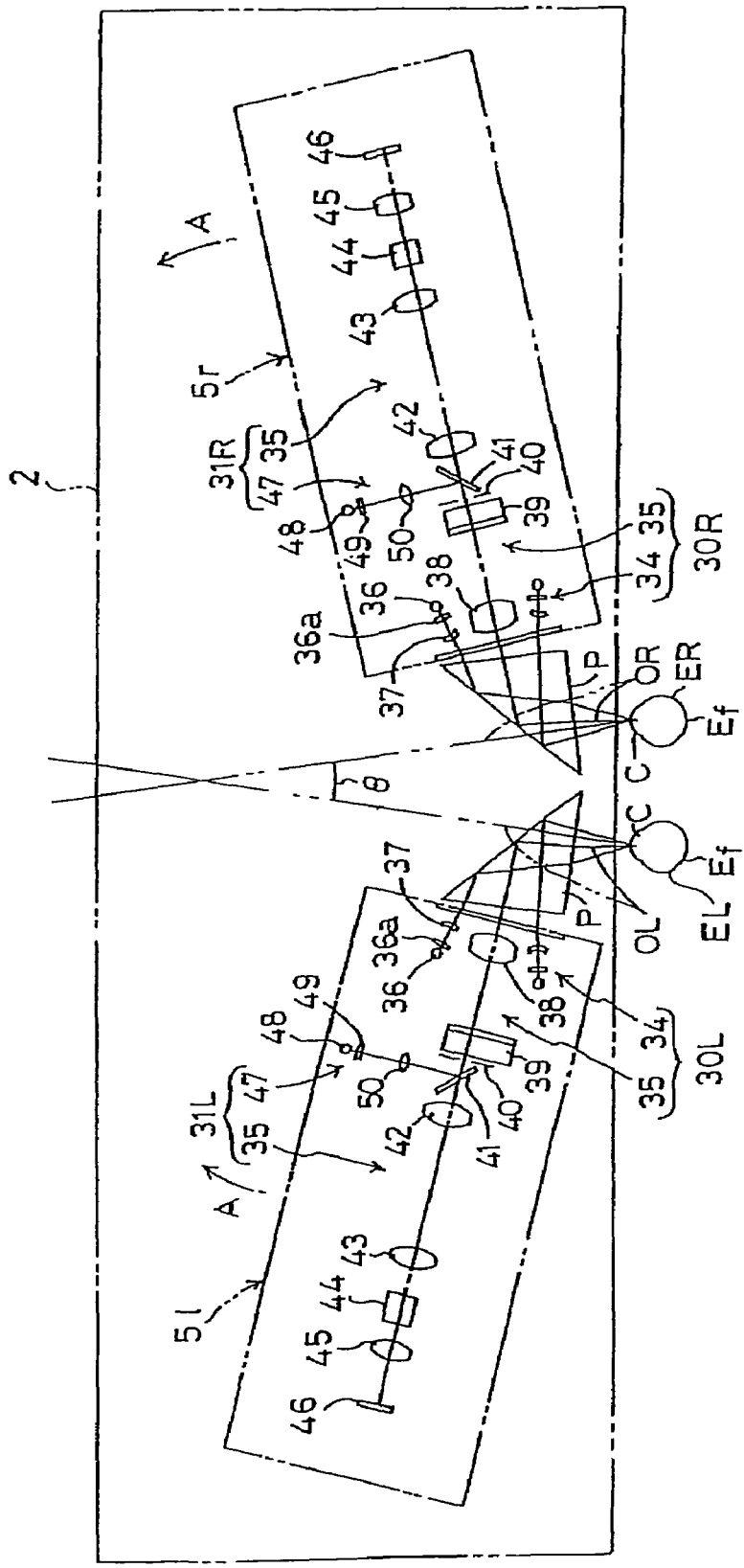
FIG. 3 is an explanatory view showing an optical system of the optometric apparatus shown in FIG. 1.
Figure 4:
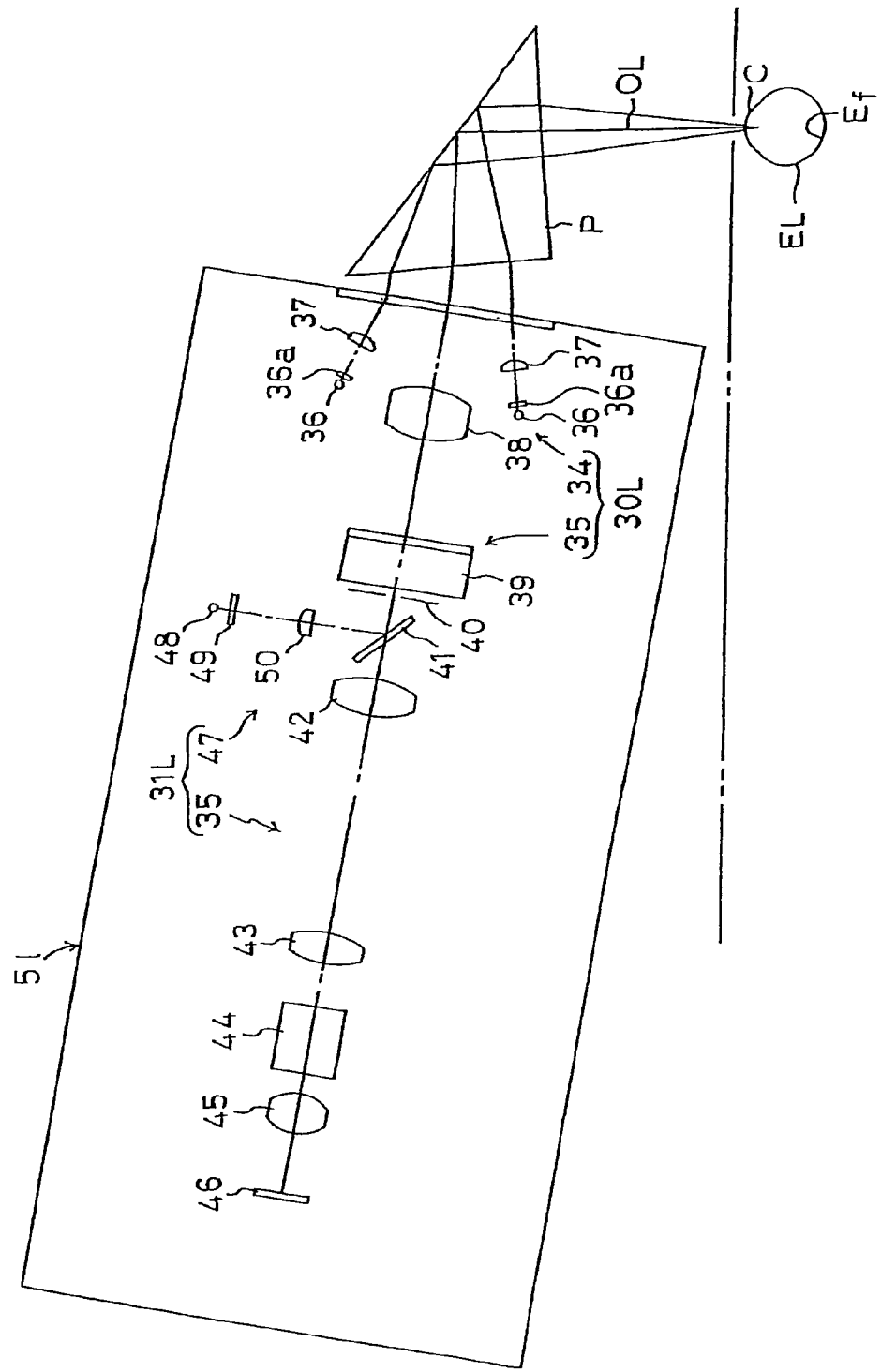
FIG. 4 is a view showing a side of a let eye of the optical system shown in FIG. 3 in an enlarged manner.
Figure 5:
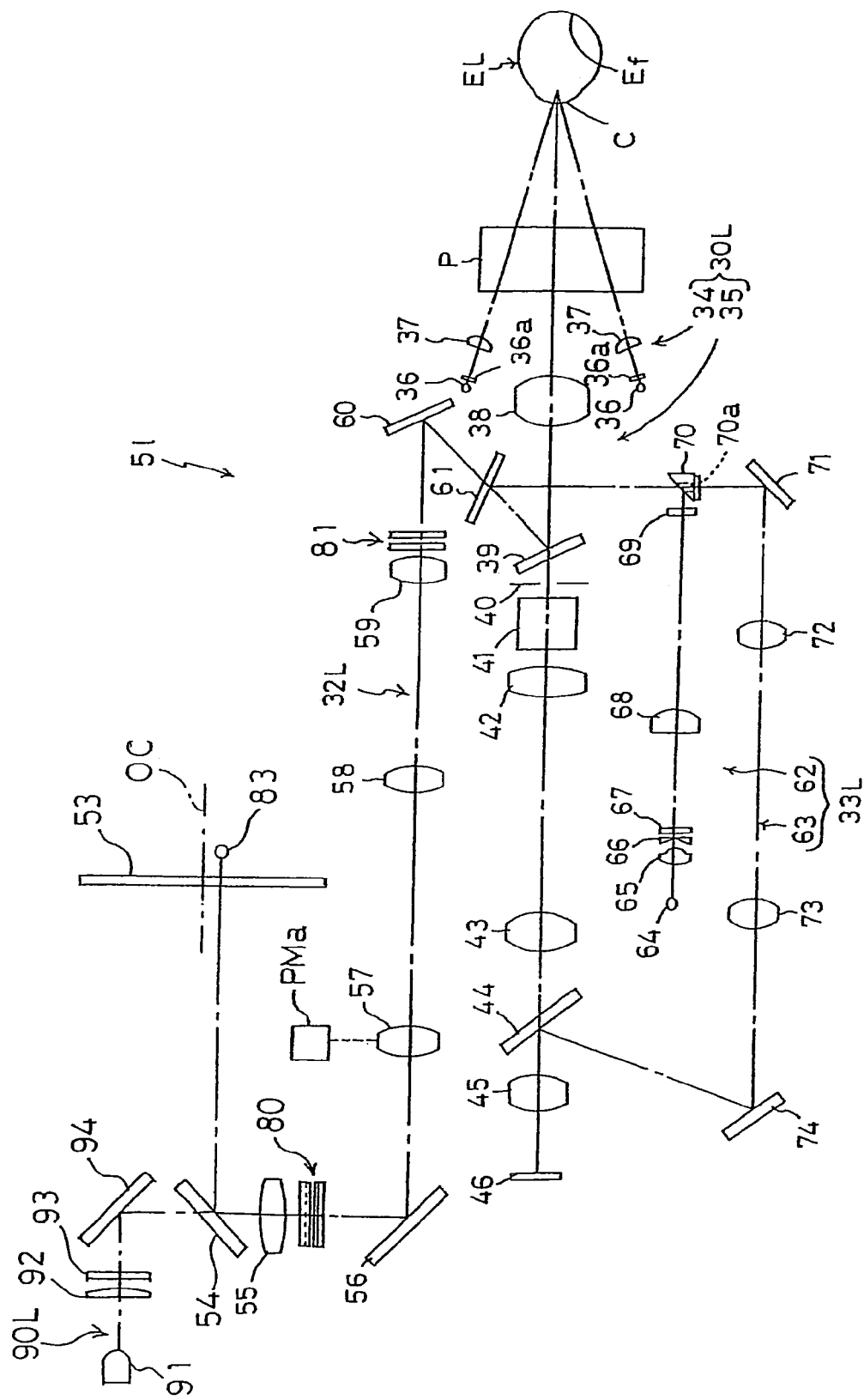
FIG. 5 is a front view of the optical system shown in FIG. 4.
Figure 6:
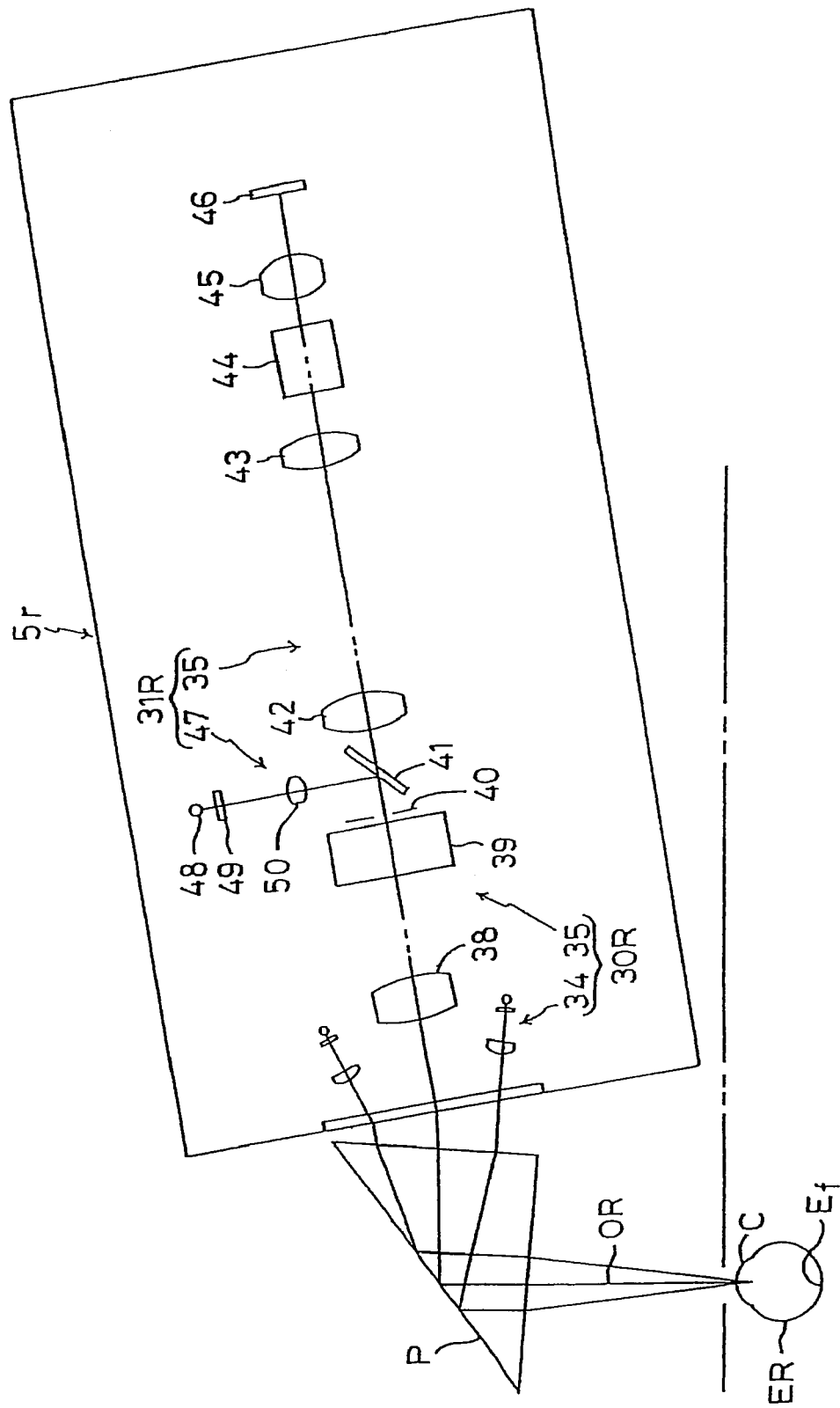
FIG. 6 is an explanatory view showing a side of a right eye of the optical system shown in FIG. 3 in an enlarged manner.
Figure 7:
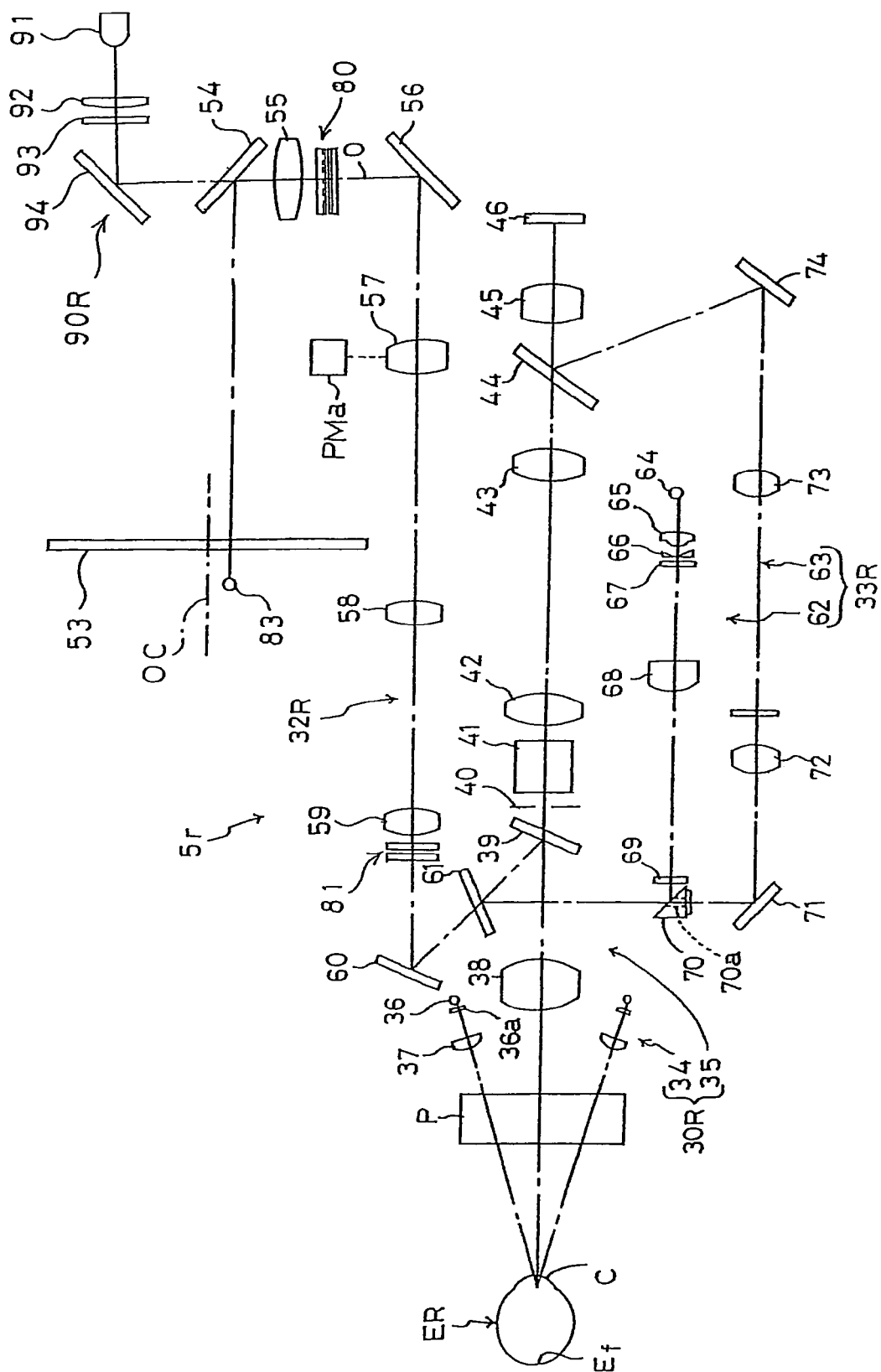
FIG. 7 is a front view of the optical system shown in FIG. 6.

The measurement optical system of the body portion 5l has an optical system 30L for photographing an anterior ocular segment, an XY alignment optical system 31L, a fixation optical system 32L, an optical system 33L for measuring a refractive power, and an optical system 90L for projecting a fusion frame, as shown in FIGS. 3 through 5. The measurement optical system of the body portion 5r has an optical system 30R for photographing the anterior ocular segment, an XY alignment optical system 31R, a fixation optical system 32R, an optical system 33R for measuring the refractive power, and an optical system 90R for projecting a fusion frame, as shown in FIGS. 3, 6 and 7.

The anterior ocular segment photography optical system 30L has an optical system 34 for illuminating the anterior ocular segment and a photographic optical system 35. The anterior ocular segment illumination optical system 34 has a light source 36 for illuminating the anterior ocular segment, an aperture stop 36a and a projection lens 37 for projecting light from the light source 36 to the anterior ocular segment of the left eye EL of eyes E to be examined.

The photographic optical system 35 has a prism P into which light reflected on the anterior ocular segment of each of the eyes E to be examined is entered, an objective lens 38, a dichroic mirror 39, an aperture stop 40, a dichroic mirror 41, relay lenses 42 and 43, a dichroic mirror 44, an imaging lens (CCD lens) 45, and a CCD (charge coupled device) 46.

The XY alignment optical system 31L has an alignment illumination optical system 47 and the photographic optical system 35 as an alignment light-receiving optical system. The alignment illumination optical system 47 has an illumination light source 48 for alignment, an aperture stop 49 as an alignment target, a relay lens 50, the dichroic mirror 41, the aperture stop 40, the dichroic mirror 39, the objective lens 38 and the prism P.

The fixation optical system 32L has a rotational target plate 53, a reflective mirror 54, a collimator lens 55, rotary prisms 80, a reflecting mirror 56, a moving lens 57, relay lenses 58 and 59, VCC (variable cross cylinder) lenses 81, a reflecting mirror 60, dichroic mirrors 61 and 39, the objective lens 38 and the prism P, as shown in FIG. 5.

In the fixation optical system 32L, the moving lens 57 moves in an optical axial direction by a pulse motor PMa in response to a refractive power of each eye to be examined, to enable the eyes E to perform fixation foggy.

Figure 8:
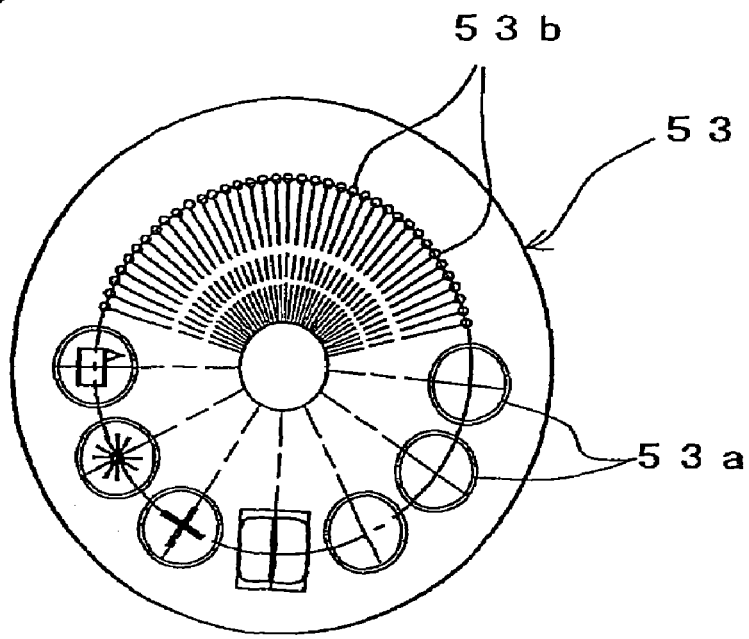
FIG. 8 is an explanatory view showing a rotational target plate in FIGS. 5 and 7.

The rotational target plate 53 has a circular plated shape of a diameter of about 60 mm as shown in FIG. 8, and is rotated about an axis OC by a device 82 (see FIG. 10) for driving the rotational target plate 53. Meanwhile, in FIGS. 5 and 7, although the axis OC is offset from an optical axis of the reflective mirror 54, the axis may be coaxial with the optical axis of the refractive mirror. A plurality of large target charts 53a (viewing angle 9.1°) on which scenery charts or the like are depicted and a plurality of small target charts 53b (viewing angle 1.2°), on which targets of Landolt rings or the like are depicted are provided to space peripherally on an outer peripheral portion of the rotational target plate 53. The target charts 53a and 53b positioned on the optical axis of the reflective mirror 54 are illuminated by a light source 83 and projected and the projected targets are adapted to be changed by rotation of the rotational target plate 53.

The optical system 33L for measuring the refractive power has an optical system 62 for projecting measuring light flux and an optical system 63 for receiving the measuring light flux. The optical system 62 for projecting the measuring light flux has a light source 64 for measurement for an infrared LED or the like, a collimator lens 65, a conical prism 66, a ring target 67, a relay lens 68, a ring shaped aperture stop 69, a perforated prism 70 having at a center thereof light permeable hole 70a, the dichroic mirrors 61 and 39, the objective lens 38 and the prism P.

On the other hand, the optical system 63 for receiving the measuring light flux has the prism P for receiving light reflected on the findus Ef of each of the examined eyes E, the objective lens 38, the dichroic mirrors 61 and 39, the light permeable hole 70a of the perforated prism 70, a reflective lens 71, a relay lens 72, a moving lens 73, a reflective lens 74, the dichroic mirror 44, the imaging lens 45 and the CCD 46.

Figure 9:
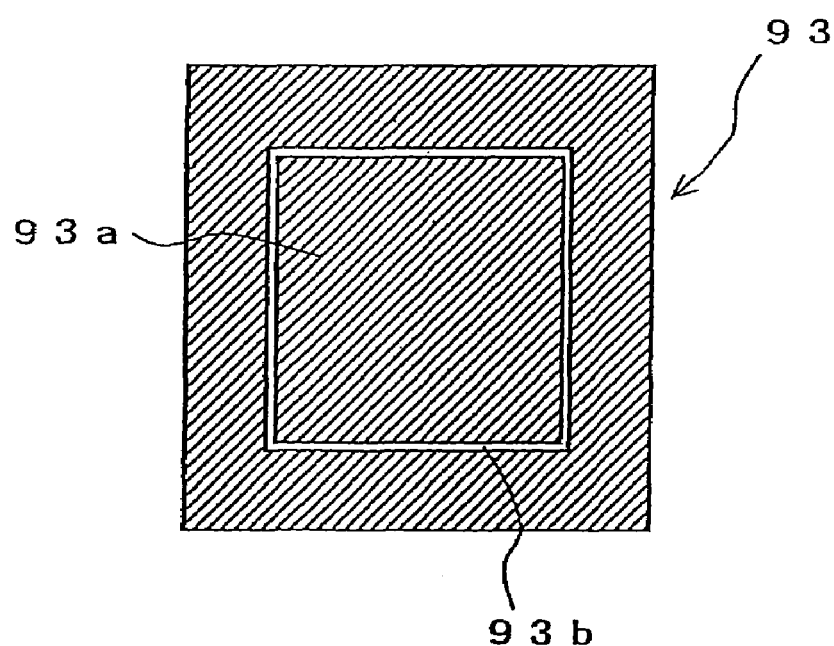
FIG. 9 is an explanatory view showing a fusion frame chart in FIGS. 5 and 7.

The optical system 90L for projecting the fusion frame has an LED 91, a collimator lens 92, a chart 93 for the fusion frame, a reflecting mirror 94, the reflective mirror 54, the collimator lens 55, the rotary prism 80, the reflective mirror 56, the moving lens 57, the relay lenses 58 and 59, the VCC lenses 81, the reflecting mirror 60, the dichroic mirrors 61 and 39, the objective lens 38 and the prism P. The LED 91, collimator lens 92, fusion frame chart 93 and reflective mirror 94 constitute means for projecting a fusion pattern for the left eye, and the fusion frame chart 93 has a light shielding part 93a and a rectangular transmitting part 93b, as shown in FIG. 9.

Although the measurement optical system of the body portion 5r is similar to the measurement optical system of the body portion 5l and therefore a detailed description thereof is omitted, an optical system 30R for photographing an anterior ocular segment, an XY alignment optical system 31R, a fixation optical system 32R, an optical system 33R for measuring a refractive power and an optical system 90R for projecting a fusion frame correspond to the optical system 30L for photographing the anterior ocular segment, the XY alignment optical system 31L, the fixation optical system 32L, the optical system 33L for measuring the refractive power and the optical system 90L for projecting the fusion frame, respectively.

The rotary prism 80 in the body portion 5r differs from the rotary prism 80 in the body portion 5l in that it is offset 90° to the optical axis.

As a control system for the optometric apparatus 2, an arithmetic control circuit 63c for controlling control circuits 62l and 62r of the body portions 5l and 5r, as shown in FIG. 10.

A tilting detection sensor 12b for detecting tilting operation of the lever 6h, the button 6g, and a rotation sensor 12c for detecting rotating operation around the axis of the lever 12 are connected with the arithmetic control circuit 63c. Liquid crystal displays 64l and 64r, and a monitor device 64q are also connected with the operation control circuit 63. The liquid crystal display 64l is provided on the front of the body portion 5l to display an image of the anterior ocular segment of the left eye of the examinee 4. The liquid crystal display 64r is provided on the front of the body portion 5r to display an image of the anterior ocular segment of the right eye of the examinee 4. The monitor device 64q is mounted on a support 64s fixed on the base portion 5a to display procedures of use to enable the examinee itself to use the optometric apparatus 2.

If the optometric apparatus 2 is set in a shop, the monitor device 64q is turned on, according to the entrance to a shop by an examinee 4, by the arithmetic control circuit 63c and examination items, such as sex, age, wearing of spectacles/contact lens or not, etc. are displayed on the monitor device 64q. According to the examination items, when the examinee replies in a touch panel type, an image for explaining the operational procedures of the optometric apparatus 2 is displayed on the monitor device 64q.

When the examinee 4 sits then down on the chair 3, places the jaw on the jaw receiver 6d and abuts the forehead with the forehead receiver 6c, the arithmetic control circuit 63c lights the light source 36 for illuminating the anterior ocular segment, the illumination light source 48 for alignment and the light source 83 for projecting the target, in the body portions 5l and 5r for performing auto-alignment for the left eye EL and the right eye ER of the examinee 4.

Figure 11:
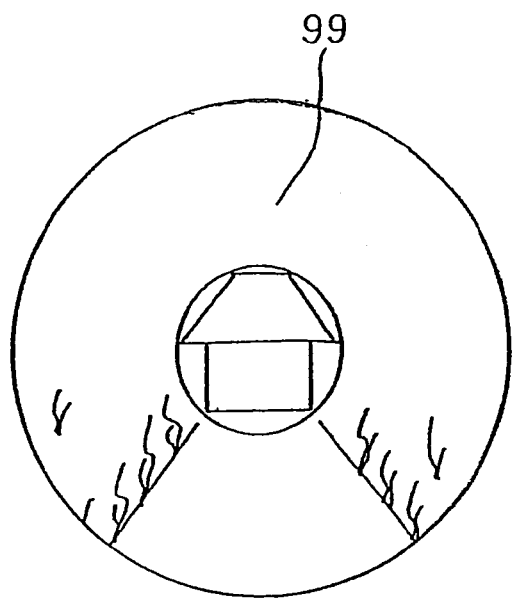
FIG. 11 is an explanatory view showing a chart of land scope displayed by the rotational plate.

Light from the light source 83 transmits the target chart 53a on which the scenery charts 99 are depicted, in the rotational target plate, as shown in FIG. 11, and then is projected, through the reflective mirror 54, the collimator lens 55, the rotary prisms 80, the reflecting mirror 56, the moving lens 57, the relay lenses 58 and 59, the VCC (variable cross cylinder) lenses 81, the reflecting mirror 60, the dichroic mirrors 61 and 39, the objective lens 38 and the prism P, on the fimdus Ef of each of the examined eyes E (both the left eye EL and right eye ER, similarly hereinafter) of the examinee 4.

The arithmetic control circuit 63c controls to drive rightward and leftward the body portions 5l and 5r into an initial setting potion by the XYZ driving mechanism 27 in such a manner that a center distance (a distance between the optical axes OL and OR, see FIG. 3) between the prisms P and P of the body portions 5l and 5r is 66 mm which is an average distance (PD value) between pupils of adults. On the other hand, the examinee 4 adjusts a height of the jaw receiver 6d so that the scenery charts 99 as the fixation target can be seen.

The illumination light from each of the light sources 36 is projected through the aperture stop 36a, and the projection lens 37 on the examined eye E, whose anterior ocular segment is illuminated. Light reflected on the anterior ocular segment of each of the examined eyes E is projected through the prism P, the objective lens 38, the dichroic mirror 39, the aperture stop 40, the dichroic mirror 41, the relay lenses 42 and 43, the dichroic mirror 44, the imaging lens 45, on the CCD 46, and the images of the anterior ocular segments of the eyes E are focused on the CCD 46. The control circuit 62l is configured to display the image EL' of the anterior ocular segment of the left eye EL based on an output signal from the CCD 46 on the liquid crystal display 64l, and the control circuit 62r is configured to display the image ER' of the anterior ocular segment of the of the left eye ER based on an output signal from the CCD 46 on the liquid crystal display 64r (see FIG. 12).

On the other hand, alignment flux from each illumination light source 48 is projected, through the aperture stop 49 as the alignment target, the relay lens 50, the dichroic mirror 41, the aperture stop 40, the dichroic mirror 39, the objective lens 38, and the prism P, on the cornea C of each of the eyes E. Light reflected on each cornea C is focused through the prism P, the objective lens 38, the dichroic mirror 39, the aperture stop 40, the dichroic mirror 41, the relay lenses 42 and 43, the dichroic mirror 44, and the imaging lens 45, on the CCD 46 to form a luminescent spot image EP from the cornea C on the CCD 46.

The control circuits 62l and 62r display on the liquid crystal displays 64l and 64r, the luminescent spot images EP, together with the images of the anterior ocular segments of the examined eyes E, based on the output signal from the CCD 46.

The control circuit 62l drives the X directional driving device 26 and the Y directional device 20 so that the signal of the luminescent spot image EP from the CCD 46 enters within a predetermined range S of the center of the CCD 46, that is to say, in the direction where the optical axis of the left eye EL of the examinee 4 matches with the center (optical axis OL) of the prism P of the body portion 5l. With this driving, the control circuit 62l stops the operation of the X and Y directional driving devices 26 and 20 when the optical axis OL of the left eye EL of the examinee 4 enters an allowable range S approximately matching with the center of the prism P of the body portion 5l (optical axis OL) to complete the XY alignment for the left eye EL of the body portion 5l.

When the XY alignment for the left eye EL of the body portion 5l is completed, the control circuit 62l drives the Z directional driving device 24 together with the X and Y directional driving device 26 and 20 so that the luminescent spot image EP of the CCD 46 becomes clear to move the body portion 5l in the direction of the optical axis OL (forward and backward direction). When it is detected that certain degree of clearness of the luminescent spot image EP of the CCD is acquired, the control circuit 62l stops the driving of the Z directional driving device 24, assuming that the Z alignment has been completed.

Moreover, the control circuit 62r drives the X directional driving device 26 and the Y directional device 20 so that the signal of the luminescent spot image EP from the CCD 46 enters within the predetermined range S of the center of the CCD 46, that is to say, in the direction where the optical axis of the right eye ER of the examinee 4 matches with the center (optical axis OR) of the prism P of the body portion 5r. With this driving, the control circuit 62r stops the operation of the X and Y directional driving devices 26 and 20 when the optical axis of the right eye ER of the examinee 4 enters an allowable range S approximately matching with the center of the prism P of the body portion 5r to complete the XY alignment for the right eye ER of the body portion 5l.

When the XY alignment for the left eye ER of the body portion 5r is completed, the control circuit 62r drives the Z directional driving device 24 together with the X and Y directional driving device 26 and 20 so that the luminescent spot image EP of the CCD 46 becomes clear, to move the body portion 5r in the direction of the optical axis OR (forward and backward direction). When it is detected that certain degree of clearness of the luminescent spot image EP of the CCD is acquired, the control circuit 62r stops the driving of the Z directional driving device 24, assuming that the Z alignment has been completed.

Figure 12A:
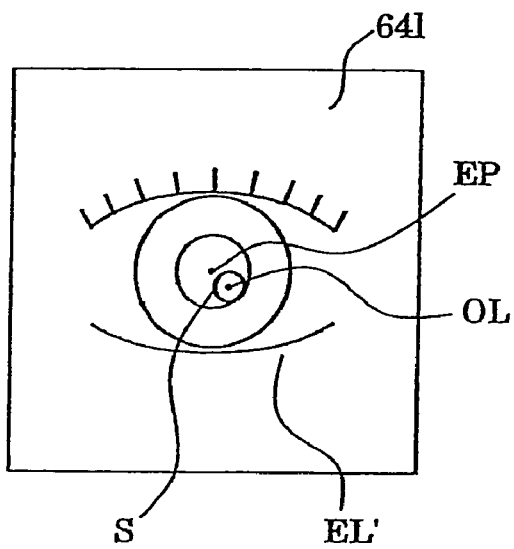
FIG. 12(a) is a view showing an image of an anterior ocular segment displayed on a liquid crystal display on a front of a body portion for the left eye.
Figure 12B:
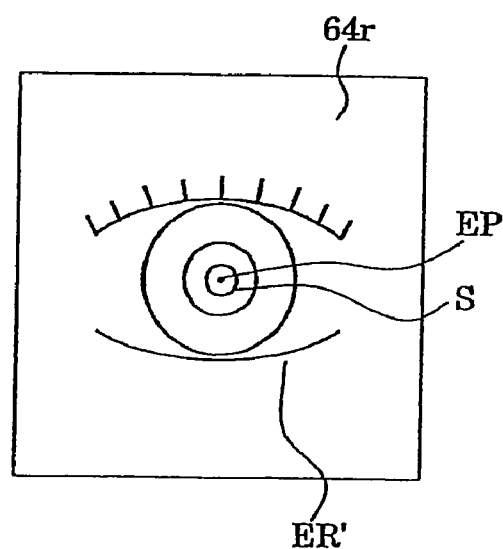
FIG. 12(b) is a view showing an image of an anterior ocular segment displayed on a liquid crystal display on a front of a body portion for the right eye.

Meanwhile, FIG. 12 shows the state where the luminescent spot image EP of the right eye EL enters the predetermined range S and the luminescent spot image EP of the left eye ER does not enter the predetermined range S.

When the auto-alignment is completed, the arithmetic control circuit 63c operates and controls the control circuit 62l and the control circuit 62, respectively, lights the light sources 64 and 64 to initiate a subjective measurement of eyesight for the right eye ER (far point inspection: in which a distance (distance of the eye inspection) between the eye to be examined of the examinee 4 and the target for the eye inspection is 5 m).

The arithmetic control circuit 63c, first, lights the light source 83 in the body portion 5r to display the Landolt ring of the value 0.1 of vision on the rotational target plate 53, and does not light the light source 83 in the body portion 5l to delete all displays for the left eye EL. The arithmetic control circuit guides to the examinee 4 that the lever 6h is fallen down toward a cutting portion of the Landolt ring and if the cutting portion cannot be recognized, the button 6g is pressed, and presents the Landolt ring of the value 0.2 of vision when the examinee 4 falls down the lever 6h in a correct direction and another Landolt ring of the value 0.1 of vision when the examinee 4 falls down the lever 6h in an incorrect direction or presses the button 6g.

For the other Landolt rings, when the examinee 4 falls down the lever 6h in the incorrect direction or presses the button 6g, the arithmetic control circuit 63c memories a value of vision of the examinee 4, which is less than 0.1, in a storing device (not shown). For the other Landolt rings, when the examiner 4 falls down the lever 6h in the correct direction, the arithmetic control circuit 63c presents the Landolr ring of the value 0.2 of vision, decides the value of vision of the examinee 4 in accordance with the similar procedures hereinafter.

Here, presents of four times at a maximum are performed for a Landolt ring of certain value of vision, for Landolt rings of each value of vision, when the lever 6h is fallen down in the correct direction three times, it is judged that the examinee 4 has the value of vision, while, an examiner is settable optionally the number of a correct answer (or an incorrect answer for lowering the value of vision of the Landolt ring) for raising the value of vision of the Landolt ring. On the change of the Landolt ring, the rotational target plate 53 rotates rightward and leftward as viewed from the examinee 4.

Subsequently, the arithmetic control circuit 63c lights the light source 83 in the body portion 5l to display the Landolt ring on the rotational target plate 53, and does not light the light source 83 in the body portion 5r to delete all displays for the right eye ER, performs the subjective measurement of vision for the left eye EL, as described above.

Figure 13A:
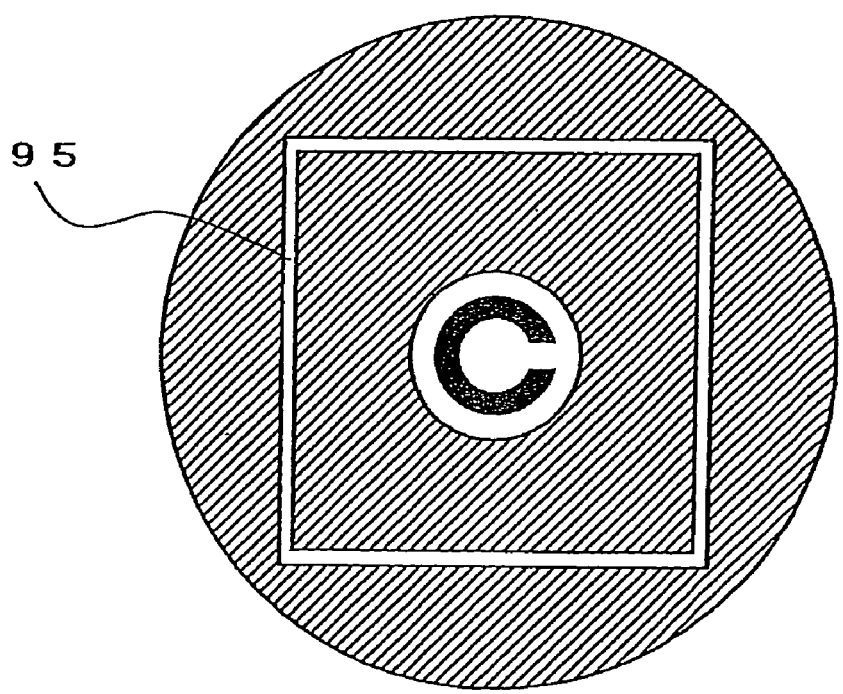
FIG. 13(a) is an explanatory view showing an example in which a fusion frame is displayed about a Landolt ring of a relatively low value of vision.
Figure 13B:
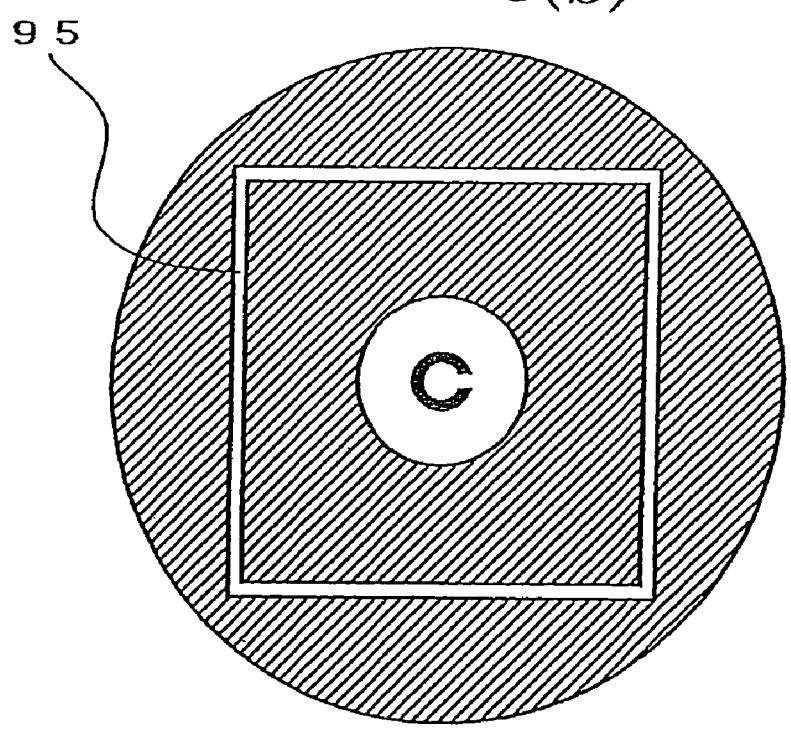
FIG. 13(b) is an explanatory view showing an example in which the fusion frame is displayed about a Landolt ring of a relatively low value of vision.

Further, the arithmetic control circuit 63c displays the same Landolt rings in the body portions 5l and 5r on the rotational target plate 53, and performs the subjective measurement of vision for both eyes as described above, while at that time, the fusion frame 95 is presented to the examinee 4 to surround the Landolt ring as shown in FIG. 13. In the present mode, an angle of vision of the fusion frame 95 is 8.9° in vertical and is 8.2° in horizon, and the fusion frame has a size of a degree inscribing in an outer shape of the target chart 53a. Because the angle of vision of the fusion frame is larger (12°) than that of the target chart 53b, the fusion frame 95 is formed on a mask portion of an outer section of the target chart 53b, when viewed from the examinee 4.

The fusion frame 95 is projected by the optical systems 90L and 90R for projecting the fusion frame. More specifically, light emitted from the LED 91 is passed through the collimator lens 92 and thereafter is entered into the fusion frame chart 93. Light (light passing through the transmitting part 93b) forming a framed shape from the fusion frame chart 93 is reflected on the reflective mirror 94 and then transmits the reflective mirror 54, and passing through the collimator lens 55, the rotary prism 80, the reflective mirror 56, the moving lens 57, the relay lenses 58 and 59, the VCC lens 81, the reflective lens 60, the dichroic mirrors 61 and 39, the objective lens 38, and the prism P, the fusion frame 95 is presented on the examined eyes E.

By the way, the fusion frame 95 assists a fusion of the examinee 4, for example, if the Landolt rings presented in the body portions 5l and 5r are relatively large as the time that the value of vision is 0.1 (as in case shown in FIG. 13,), certain degree of fusion operation can be expected for the Landolt rings itself, while, if the Landolt rings presented in the body portions 5l and 5r are relatively small as the time that the value of vision is 1.0 and the fusion operation of the Landolt rings itself is weak (as in case shown in FIG. 13b), the fusion operation of the fusion frame 95, which is larger than the Landolt rings and is easy to see, is more effectively.

Figure 14:
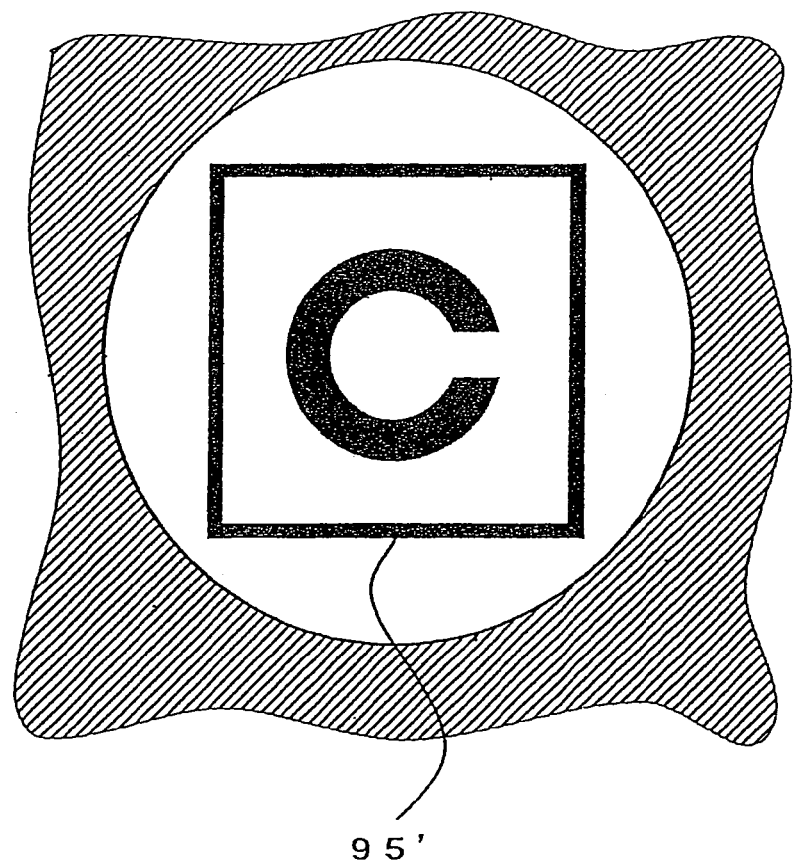
FIG. 14 is an explanatory view showing an example in which the fusion frame is projected about a target and inside a mask.

Consequently, the fusion frame 95 is presented in a case that it is more than a predetermined value of vision (vision value of the Landolt rings) and in which the effect thereof significantly appears and may not be presented in a case that is less than the predetermined value. With such construction, a fusion frame 95' is displayed inside the mask together with the Landolt ring as shown in FIG. 14, for example, and in case of a structure that the LED 91, the collimator lens 92, the fusion frame chart 93 and the reflective lens 94 are not provided, a space is set effectively than that of provision of fusion frames on peripheries of all the Landolt rings on the rotational target plate and therefore more many of Landolt rings can be provided on the rotational target plate (see FIG. 15). Meanwhile, the fusion frame can be provided on the peripheries of all the Landolt rings with a relatively small space by providing a plurality of rotational target plates in a stacked condition.

When the subjective measurement of vision is completed, the arithmetic control circuit 63c is adapted to perform the auto-alignment again, and to initiate simultaneously an objective measurement for a refracting power of each of the left and right eyes EL and ER of the examinee 4 according to the completion of the subjective measurement.

In the measurement for the refracting power, the arithmetic control circuit 63c first operates and controls the control circuits 62l and 62r and lights the light sources 64 and 64 for measurement of the body portions 5l and 5r to exit infrared measurement flux from the light sources 64 and 64.

The measurement flux from the light source 64 for measurement is led to the ring target 67 through the collimator lens 65 and the conical prism 66, in the optical system 62 for projecting the measurement flux. The ring-shaped measurement flux (ring-shaped target light) having passed the ring target 67 is projected to the findus Ef of each of the left eye EL and the right eye ER of the examinee 4 through the relay lens 68, the ring-shaped aperture stop 69, the perforated prism 70 with the through hole 70a formed at the center, the dichroic mirrors 61 and 39, the objective lens 38 and the prism P.

The ring-like measurement flux projected to the findus Ef is reflected on the fundus Ef. This reflected light forms a ring-shaped reflected image on the CCD 46, through the measurement flux light-receiving optical system 63, that is, the prism P, the objective lens 38, the dichroic mirrors 39 and 61, the through hole 70a of the perforated prism 70, the reflecting mirror 71, the relay lens 72, the moving lens 73, the reflecting mirror 74, the dichroic mirror 44, and the CCD lens 45.

A detection signal from the CCD 46 is inputted into the control circuit 62l in the body portion 5l and is inputted into the control circuit 62r in the body portion 5r. When the detection signal is inputted, the control circuit 62l and 62r measure the refracting powers of the left eye EL and the right eye ER by comparison of a shape (size) of a predetermined reference ring-shaped reflected image and a shape (size) of the ring-shaped reflected image imaged on the CCD 46.

Furthermore, although the optometric apparatus 2 is capable of objectively measuring an axial angle of an astigmatism axis and frequency of astigmatism, a measurement principle for the refracting power, the axial angle and the frequency of astigmatism is known and therefore the detailed description is omitted.

Subsequently, the arithmetic control circuit 63c performs an oblique positional inspection by presenting a cross-shaped oblique positional chart shown in FIG. 16c to the examinee 4. In the oblique positional inspection, a chart 100 on which two linear targets 100a and 100b extending rightward and leftward (horizontal direction) are arranged in the same straight line is projected on the left eye EL by the rotational target plate 53 (see FIG. 16a), a chart 101 on which two linear targets 101a and 101b extending upward and downward (vertically) are arranged in the same straight line is projected on the right eye ER by the rotational target plate 53 in the body portion 5r (see FIG. 16b). The fusion frames 95 are projected by the optical systems 90L and 90R for projecting the fusion frame, and the fusion frames 95 surround the charts 100 and 101.

In this state, the examinee 4 is asked about whether or not the four lines are visible 100a, 100b, 101a, and 101b, there are given instructions of pressing the button 6g of the lever 6h if they are visible, falling down the lever 6h rightward or leftward if the two horizontally extending linens 100a and 100b only are visible, and falling down the lever 6h forward or backward if the two vertically extending lines 101a and 101b only are visible. Here, the right eye ER is restrained if the lever 6h is fallen down rightward or leftward, and the left eye EL is restrained if the lever 6h is fallen down rightward or leftward, and therefore because the oblique positional inspection is no longer impossible, at this time the arithmetic control circuit 63c memories "oblique position: demand of detailed examination" to a storage device (not shown) and then terminates the oblique positional inspection.

On the other hand, if the button 6g of the lever 6h is pressed, the arithmetic control circuit 63c asks to the examinee whether or not an intermediate position (a central position of the chart 100) between the two horizontally extending lines 100a and 100b and an intermediate position (a central position of the chart 101) between the two vertically extending lines 101a and 101b are overlapped, and instructs to press the button 6g to the examinee, if they are overlapped. The arithmetic control circuit gives then to the examinee instructions in such a manner that if the two vertically extending lines 101a and 101b tilt toward the right relative to the two horizontally extending lines 100a and 100b, the lever 6h is fallen down rightward, and if the two vertically extending lines 101a and 101b tilt toward the left relative to the two horizontally extending lines 100a and 100b, the lever 6h is fallen down leftward. At this time, if the button 6g is pressed, the arithmetic control circuit memories "oblique position: normal" to the aforementioned storage device, and terminates the oblique positional inspection.

If the lever 6h is fallen down rightward or leftward, the arithmetic control circuit 63c rotates the rotary prism 80 of each of the body portions 5l and 5r through the control circuits 62l and 62r, and performs prism conversion of 0.25 Δ (Δ: prism diopter) in one eye and 0.50 66 in both eyes. Until the two vertically extending lines 101a and 101b come to the intermediate position of the two horizontally extending lines 100a and 100b, the lever 6h is fallen down rightward or leftward, and if the two vertically extending lines 101a and 101b arrive at the intermediate position of the two horizontally extending lines 100a and 100b, the arithmetic control circuit instructs to press the button 6g to the examinee 4.

The arithmetic control circuit 63c counts numbers that the lever 6h is fallen down rightward or leftward while deleting and adding, and obtains an amount of prism by multiplying the count number at the time the button 6g is pressed by 0.5. In other words, for example, 1 is added when the lever 6h is fallen down rightward, and 1 is subtracted when the lever is fallen down leftward. If the lever 6h fallen down rightward three times, leftward one time, and the button 6g is pressed, the count numbers at the time the button 6g is pressed is 3 (times)−1 (time)=2 (times), and the prism amount to be obtained is 2 (times) by 0.5 (Δ/time)=1 (Δ). Here, if the number in which the lever 6h is fallen rightward is large, the eye is an inner oblique position (BO), and if the number in which the lever is fallen leftward is large, the eye is an outer oblique position (BI) and therefore in the above example, the arithmetic control circuit 63c memories "horizontal oblique position: BO 1 Δ" to the storage device.

Subsequently, the arithmetic control circuit 63c asks to the examinee whether or not the intermediate position between the two horizontally extending lines 100a and 100b and the intermediate position between the two vertically extending lines 101a and 101b are overlapped, and instructs to press the button 6g to the examinee, if they are overlapped. The arithmetic control circuit gives then to the examinee instructions in such a manner that if the two vertically extending lines 101a and 101b tilt toward the up relative to the two horizontally extending lines 100a and 100b, the lever 6h is fallen down upward, and if the two vertically extending lines 101a and 101b tilt toward the down relative to the two horizontally extending lines 100a and 100b, the lever 6h is fallen down downward. At this time, if the button 6g is pressed, the arithmetic control circuit memories "vertical oblique position: 0 Δ" to the aforementioned storage device, and terminates the oblique positional inspection.

If the lever 6h is fallen down upward, the arithmetic control circuit 63c judges that the right eye ER is a BD prism and the left eye is a BU prism. Until the two vertically extending lines 101a and 101b come to the intermediate position of the two horizontally extending lines 100a and 100b, the lever 6h is fallen down upward or downward, and if the two vertically extending lines 101a and 101b arrive at the intermediate position of the two horizontally extending lines 100a and 100b, the arithmetic control circuit instructs to press the button 6g to the examinee.

The arithmetic control circuit 63c counts numbers that the lever 6h is fallen down upward or downward while deleting and adding, and obtains an amount of prism by multiplying the count number at the time the button 6g is pressed by 0.5. In other words, for example, 1 is added when the lever 6h is fallen down rightward, and 1 is subtracted when the lever is fallen down leftward. If the lever 6h fallen down upward three times, downward one time, and the button 6g is pressed, the count numbers at the time the button 6g is pressed is 3 (times)−1 (time)=2 (times), and the prism amount to be obtained is 2 (times) by 0.5 (Δ/time)=1 (Δ). Here, if the number in which the lever 6h is fallen upward is large, the right eye is an upper oblique position, and if the number in which the lever is fallen downward is large, the left eye is an upward oblique position and therefore in the above example, the arithmetic control circuit 63c memories "vertical oblique position: BD 1 Δ" to the storage device and terminates the oblique positional inspection.

By the way, the fusion frames 95 are projected peripherally of the charts 100 and 101, respectively, as shown in FIGS. 16(a) and (b) and the fusion frames 95 are seen to overlap as viewed by the both eyes, as shown in FIG. 16(c). However, if the fusion frames 95 are not displayed, a positional relationship between the two horizontal lines 100a, 100b and the two vertical lines 101a, 101b is seen in a deviated state even if the examinee 4 has an oblique position of an degree that there is no problem in everyday life, as a result the oblique position is detected sharply. This results from the fact that a real object is not watched with the both eyes, separate charts are projected through two right and left separated optical systems and one virtual object (virtual chart) that the charts are combined is watched with the both eyes. On the contrary, in the optometric apparatus 2, the same fusion frames 95 projected in the left and right body portions 5l and 5r urge the fusion to the examiner 4 and therefore even if the examinee 4 has an oblique position of an degree that there is no problem in everyday life, the fusion of the charts 100 and 101 can be performed and thereafter the proceeding of the inspection is also not disturbed (in addition, it is considered in the specification that a case, which is not possible to perform the fusion by the fusion frame is not primarily an eye squinting, is an advanced degree of oblique position or eye squinting.

The arithmetic control circuit 63c makes it possible to perform a R/G inspection every one eye as an objective inspection to acquire a spherical diopter power, and to perform a cross cylinder inspection to acquire an angle of astigmatism axis, and a degree of astigmatism, other than the measurement of vision and the oblique positional inspection as described above.

Figure 17:
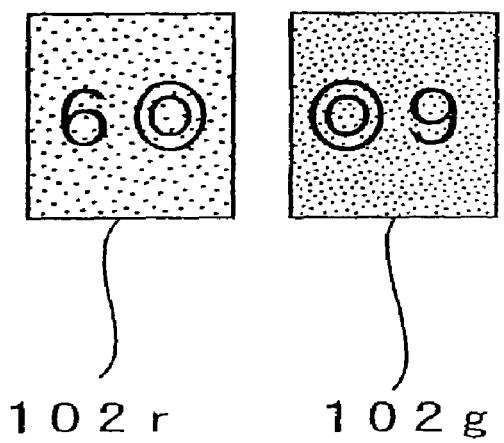
FIG. 17 is an explanatory view showing a chart used in a R/G test.

In the R/G inspection, the arithmetic con troll circuit 63c presents a left target 102r in which numeral character is written on red ground color and a right target 102g in which numerical character is written on green ground color, to the examinee 4 as shown in FIG. 17. When the examinee 4 falls down the lever 6h in a direction in which the numerical characters are visible clearly, the arithmetic control circuit 63c moves the moving lens 57 inside the body portion 5l in such a manner that the spherical diopter power changes by −0.25 D to adjust a diopter scale, if the lever 6h is fallen down in the direction of red color (left direction), and the arithmetic control circuit moves the moving lens 57 in such a manner that the spherical diopter power changes by +0.25 D to adjust the diopter scale, if the lever 6h is fallen down in the direction of green color (right direction).

At the time the operational direction of the lever 6h is switched from the left (red) to the right (green) or from the right (green) to the left (red), the R/G inspection is terminated, and the spherical diopter power in a state that the red color is visible well, a state that the green is visible well or a state that the color determined according to a method that the lever is fallen down is visible well, is stored in the storage device. Meanwhile, a moving step of the moving lens 57 may not be a unit of 0.25 D and the examiner is able to set it optionally.

Figure 18:
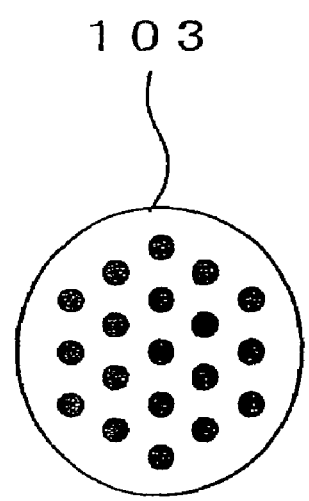
FIG. 18 is an explanatory view showing a chart used in a cross-cylinder test.
Figure 19:
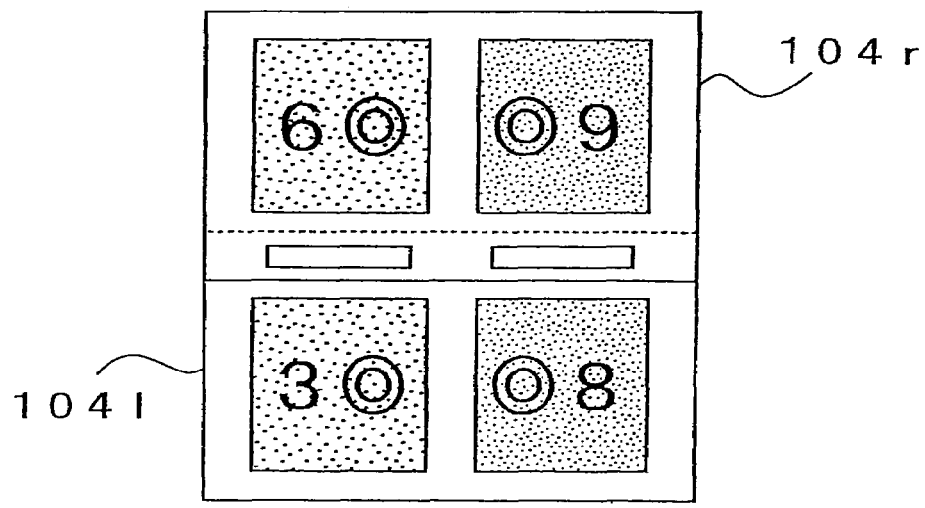
FIG. 19 is an explanatory view showing a chart used in taking a balance of the both eyes

In the cross cylinder inspection, the Landolt ring or the cross cylinder chart 103 as shown in FIG. 18 is presented to the examinee 4 as the target, and the astigmatism axis is first measured.

In the measurement for the astigmatism axis, the arithmetic control circuit 63c rotates the variable cross cylinder or the VCC lens 81 for compensating the astigmatism inside the body portion 5l or 5r, and adds ±0.25 to the degree of astigmatism of the examined eyes in directions of ±45° respectively, based on the axial angles by the objective measurement.

In other words, the arithmetic control circuit 63c first rotates the variable cross cylinder in such a manner that +0.25 D is added to the degree of astigmatism by the objective measurement with respect to the direction of +45°, based on the axial angle by the objective measurement, and −0.25 is added to the degree of astigmatism by the objective measurement with respect to the direction of −45°, based on the axial angle by the objective measurement, and then presents to the target of the cross cylinder chart 103 and so on to the examinee 4, guides that the above state is "1" by voice. Subsequently, the arithmetic control circuit 63c rotates the variable cross cylinder in such a manner that −0.25 D is added to the degree of astigmatism by the objective measurement with respect to the direction of +45°, based on the axial angle by the objective measurement, and +0.25 is added to the degree of astigmatism by the objective measurement with respect to the direction of −45°, based on the axial angle by the objective measurement, and then presents to the target of the cross cylinder chart 103 and so on to the examinee 4, guides that the above state is "2" by voice.

The arithmetic control circuit guides the lever 6h in such a manner that it is fallen down leftward at the time of the state "1", if the target is visible well, and it fallen down rightward at the time of the state "2", if the target is visible well, and rotates the variable cross cylinder by a predetermined amount (for example, 10°) so that the degree of astigmatism in the direction in which the examinee 4 falls down the lever 6h (direction in which the examinee replies to as is well visible) is reduced.

Thereafter, the arithmetic control circuit 63c repeats the similar procedures and terminates the eye inspection at the time the operational direction of the lever 6h is switched from the left to the right or from the right to the left, memories a value of the axial angle of the astigmatism axis at that time to the storage device. Meanwhile, a rotational amount or a predetermined amount of the variable cross cylinder may be changed by setting of the examiner or the degree of astigmatism by the objective measurement, it is possible to increase accuracy of the eye inspection (accuracy of the axial angle to be acquired) by lessening the rotational amount.

When the axial angle of the astigmatism axis is decided, the arithmetic control circuit 63c then initiates measurement of the degree of astigmatism. The target used at that time is similar to that in case of obtaining the axial angle, the arithmetic control circuit 63c rotates the variable cylinder in such a manner that −0.25 D is added to the degree of astigmatism by the objective measurement with respect to the direction of the obtained axial angle, and +0.25 is added to the degree of astigmatism with respect to the direction perpendicular to the above direction, presents the target to the examinee 4 and guides that this case is 1 by voice. Moreover, the arithmetic control circuit 63c rotates the variable cross cylinder in such a manner that +0.25 D is added to the degree of astigmatism by the objective measurement with respect to the direction of the obtained axial angle, and −0.25 is added to the degree of astigmatism with respect to the direction perpendicular to the above direction, presents the target to the examinee 4 and guides that this case is 2 by voice.

The arithmetic control circuit guides the lever 6h in such a manner that it is fallen down leftward at the time of the state "1", if the target is visible well, and it fallen down rightward at the time of the state "2", if the target is visible well, and adds −0.25 D to the degree of astigmatism, if the lever 6h is fallen down leftward and adds +0.25 to the degree of astigmatism, if the lever 6h is fallen down rightward.

Thereafter, the arithmetic control circuit 63c repeats the similar procedures and terminates the cross cylinder inspection at the time the operational direction is switched from the left to the right or from the right to left, and stores the value of the degree of astigmatism at that time to the storage device. Meanwhile, the degree of astigmatism stored herein may be a value right before the operational direction of the lever 6h is switched or a value right after the operational direction of the lever 6h is switched, the examiner is settable any one of the values.

When the cross cylinder inspection is completed, the arithmetic control circuit 63c takes a balance of the spherical diopter power in each of the both eyes of the examinee 4. At this time, a balance chart for the both eyes comprising a balance chart 104r for the right eye and a balance chart 104l for the left eye is used, and an adjustment for the spherical diopter powers in the both eyes by the same method as the R/G inspection. The method is general and therefore a detailed description thereof is omitted.

By the way, in the aforementioned cross cylinder inspection, because the states 1 and 2 first are guided by voice, then a response is requested to the examinee 4 by mutual comparison of the states, there is a case that the examinee cannot judge distinction of the states 1 and 2 (one that the examinee watches is the state 1 or state 2) only by presenting merely the cross cylinder chart 103 and so on to, as shown in FIG. 18 to the examinee.

Therefore, a convenience for the examinee may be promoted by using a multi color LED emitting light of more two colors as the LED 91 and by displaying the fusion frame 95 colored pursuant to the states, together with the cross cylinder chart 103.

Figure 20:
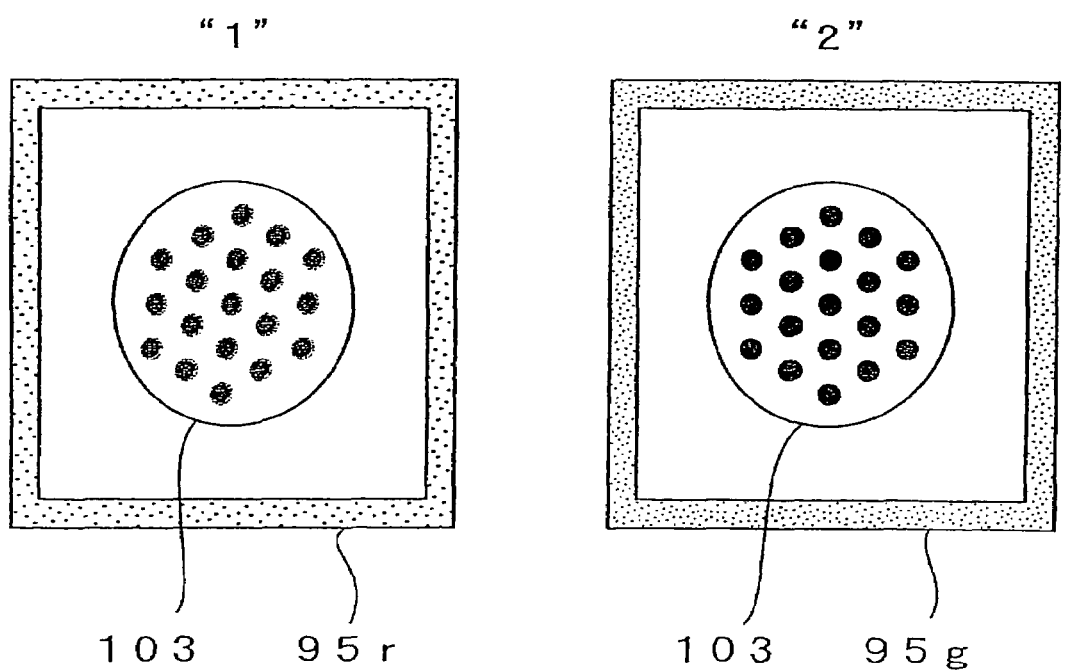
FIG. 20 is an explanatory view showing an example in which a fusion frame for distinction of a state is displayed together with the chart in FIG. 18.

In this case, the arithmetic control circuit 63c projects a red fusion frame (denoting at numeral 95r in FIG. 20) together with the cross cylinder chart 103 by lighting the LED 91 in red color at the time of the state "1", for example, and projects a green fusion frame (denoting at numeral 95g in FIG. 20) together with the cross cylinder chart 103 by lighting the LED 91 in green color at the time of the state "2", and guides to the examinee 4 that if the chart of the red color is visible well, the lever 6h is fallen down leftward and if the chart of the green color is visible well, the lever 6h is fallen down rightward.

In this way, by using the fusion frame 95 together in the cross cylinder inspection, it is possible to avoid incorrectness of the inspection result due to misconception and error of the examinee and therefore to increase accuracy of the eye inspection. Moreover, during the inspection, although it is considered that voice guide is fed out point by point in order to judge the states "1" and "2" surely to the examinee, if both the fusion frame 95 and cross cylinder chart are used as described above, the fusion frame is lighted and the voice guide can be omitted to shorten the inspection time, whereby eliminating a load to which the examinee feels during the inspection.

Figure 21:
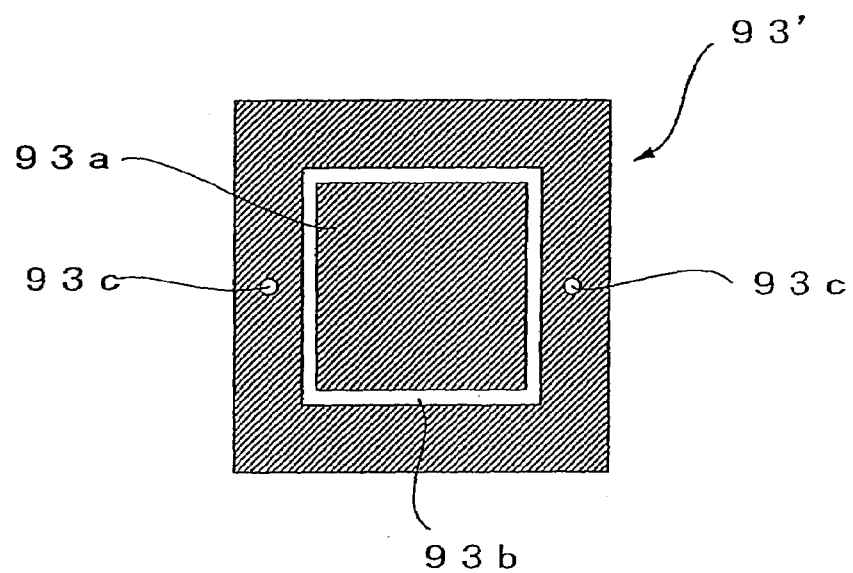
FIG. 21 is an explanatory view showing another example of the fusion frame chart.
Figure 22:
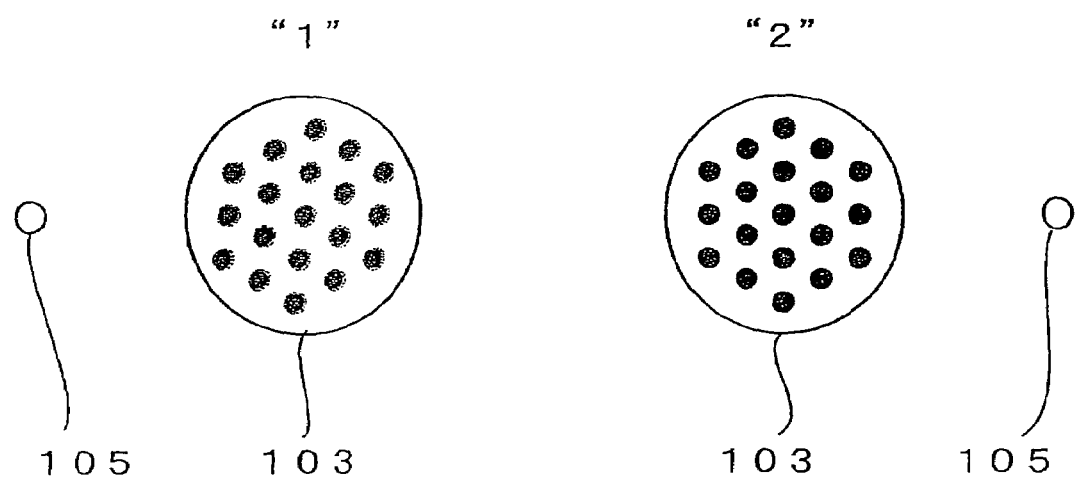
FIG. 22 is an explanatory view showing an image projected when the cross cylinder test is performed by use of the fusion frame chart as distinction of the state in FIG. 21.

In addition, considering from the viewpoint of the distinction of the states, the fusion frame 95 may be presented in only either one of the states "1", and "2", the fusion frame may not be presented in the other of the states, and the color of the fusion frame may be changed in accordance with ability of color judgment of the examined eyes. Moreover, the multi color LED as the LED 91 may not be used, instead, a color filter (not shown) may be disposed in front of the LED (between the LED 91 and the collimator lens 92) to color the fusion frame 95. Furthermore, by using a fusion frame chart 93' provided with a pair of light through portions 93c and 93c on right and left sides of a transmitted portion 93b as shown in FIG. 21, a mark 105 is projected leftward of the cross cylinder chart 103 by one of the light through portions 93c and 93c at the time of the state "1", as shown on the left side in FIG. 22, and a mark 105 is projected rightward of the cross cylinder chart 103 by the other of the light through portions 93c and 93c at the time of the state "2", as shown on the right side in FIG. 22, so that the distinction of the states is contributed.

If age of the examinee 4 is, for example, more than 45 years old, the arithmetic control circuit 63c carries out further a near point inspection. In the near point inspection, the horizontal rotary driving device 28 provided inside the driving mechanism box 5b drives to rotate the supports 5p and 5q in the opposite directions (directions of arrows A in FIG. 3) with respect to each other in a horizontal plane, a convergence angle θ defined by the optical axis OL of the optical system for the left eye in the body portion 5l and the optical axis OR of the optical system for the right eye in the body portion 5r is set in accordance with a distance for inspecting eyesight (30 cm herein, as described hereinafter). Here, the convergence angle is defined with respect to the apparatus, not the examinee 4, when the both eyes of the examinee 4 are converged pursuant to the angle, an intersecting angle of lines of sight of the both eyes is similar to the convergence angle.

Figure 23:
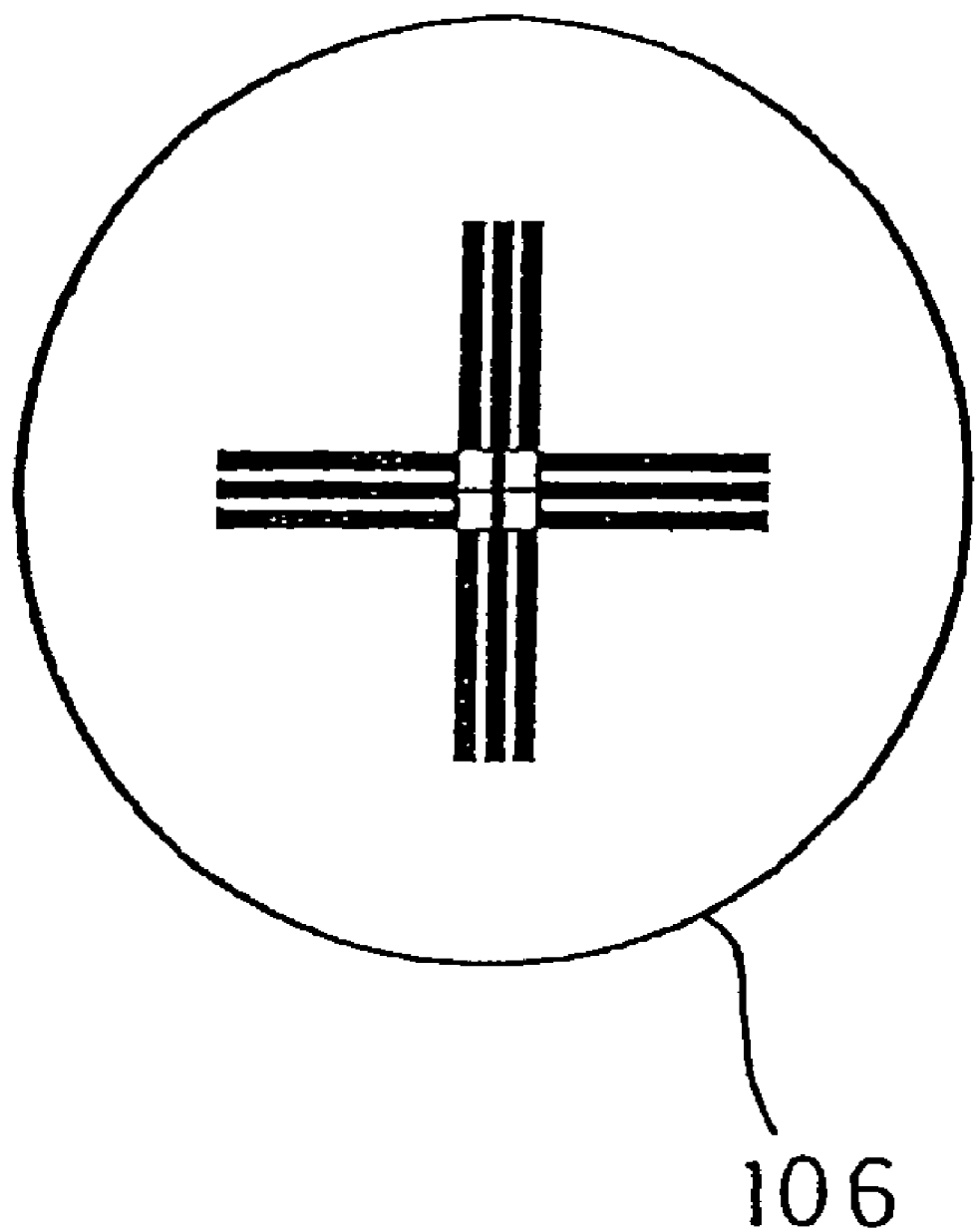
FIG. 23 is an explanatory view showing a chart used in a near point inspection.

After the setting of the convergence angle, the arithmetic control circuit 63c projects the chart 106 as shown in FIG. 23 by the rotational target plate 53 of each of the body portions 5l and 5r, and acquires a near addition power with a unit D (diopter) by whether either of the horizontal and vertical lines is visible densely. The method is known and therefore a detailed description thereof is omitted.

When the near point inspection is completed, the arithmetic control circuit 63c performs a near vision inspection (vision inspection that a distance for inspecting the vision is 30 cm). In the near vision inspection, the vision of the examinee 4 is measured in a case passing through a lens of the near addition power obtained by the near inspection, the method is the same as the subjective vision inspection as described above (however, presence of the Landolt ring is started from the value 0.5 of vision not from the value 0.1 of vision, a presented time of one target is four (4) seconds). In the near vision inspection, the fusion frame 95 is displayed peripherally of the Landolt ring when measuring the both eyes, it is possible to increase the fusion even with respect to the examinee that recognition for viewing a near place is less and the both eyes are difficult to converge or the targets are difficult to see correspondently by the both eyes, despite the convergence angle θ has been increased.

In the optometric apparatus 2 in this embodiment, because the same fusion encouragement is given by the optical system of each of the body portions 5l and 5r, the fusion of the both eyes is stimulated effectively if the examinee has light oblique position and there is affection of near sight in an instrument or tester, even if the optical systems of the body portions 5l and 5r project mutually different charts as the targets (in case of the oblique positional inspection or the like), and project mutually same charts (in case of the near vision inspection or the like), especially if a chart having a small display is projected.

Figure 15A:
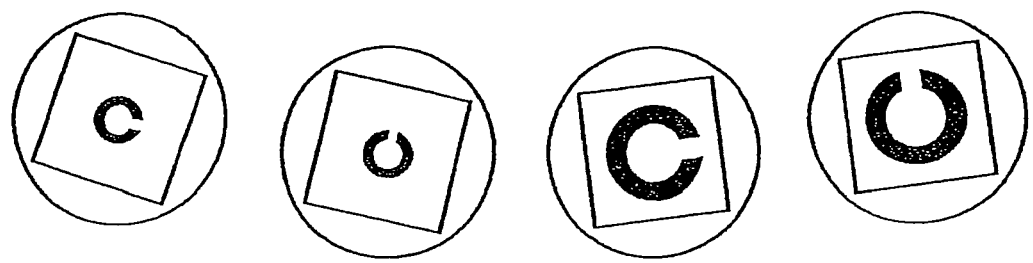
FIG. 15(a) is an explanatory view showing an example in which fusion charts are depicted about the Landolt ring of each vision value in the rotational target plate.
Figure 15B:
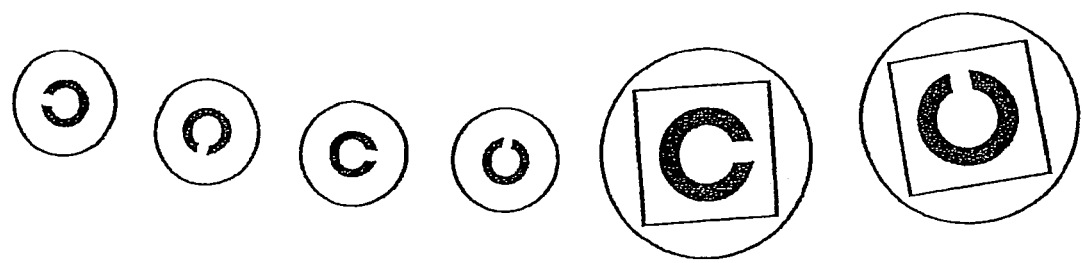
FIG. 15(b) is an explanatory view showing an example in which fusion charts are depicted about the Landolt ring of more than a predetermined vision value in the rotational target plate.

Moreover, because the fusion frame 95 is projected through the reflective mirror 54 by the optical system separated from the rotational target plate 53, and is displayed by combining with the targets of the Landolt ring and so on, the apparatus is easy to miniaturize if the fusion frames are projected simultaneously to a great number of targets, than taking a structure as shown in FIG. 15 in which the fusion frame charts are provided in the target charts.

Figure 24:
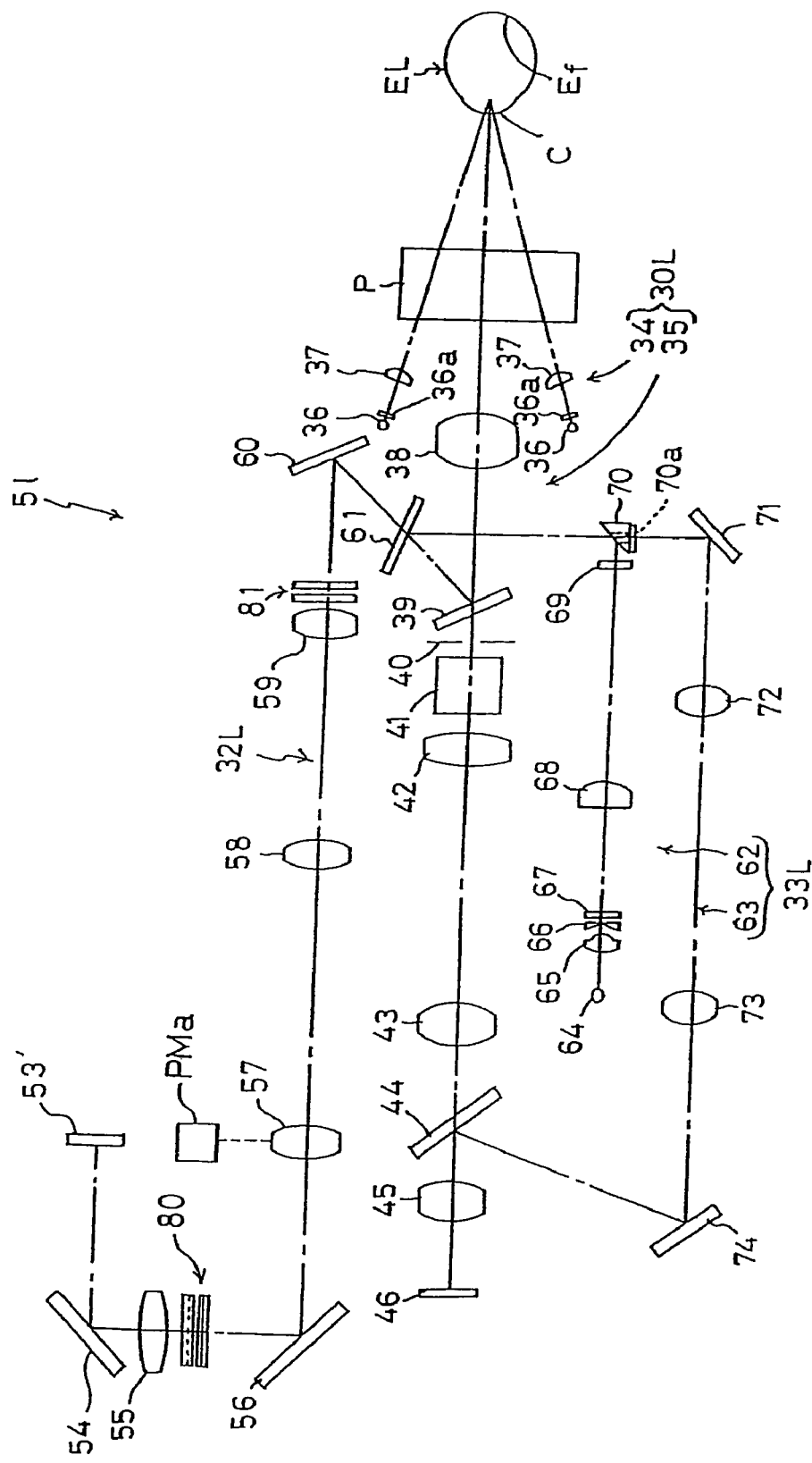
FIG. 24 is an explanatory view showing an example in which a liquid crystal display is used instead of the rotational target plate in the optical system in FIG. 5.
Figure 25:
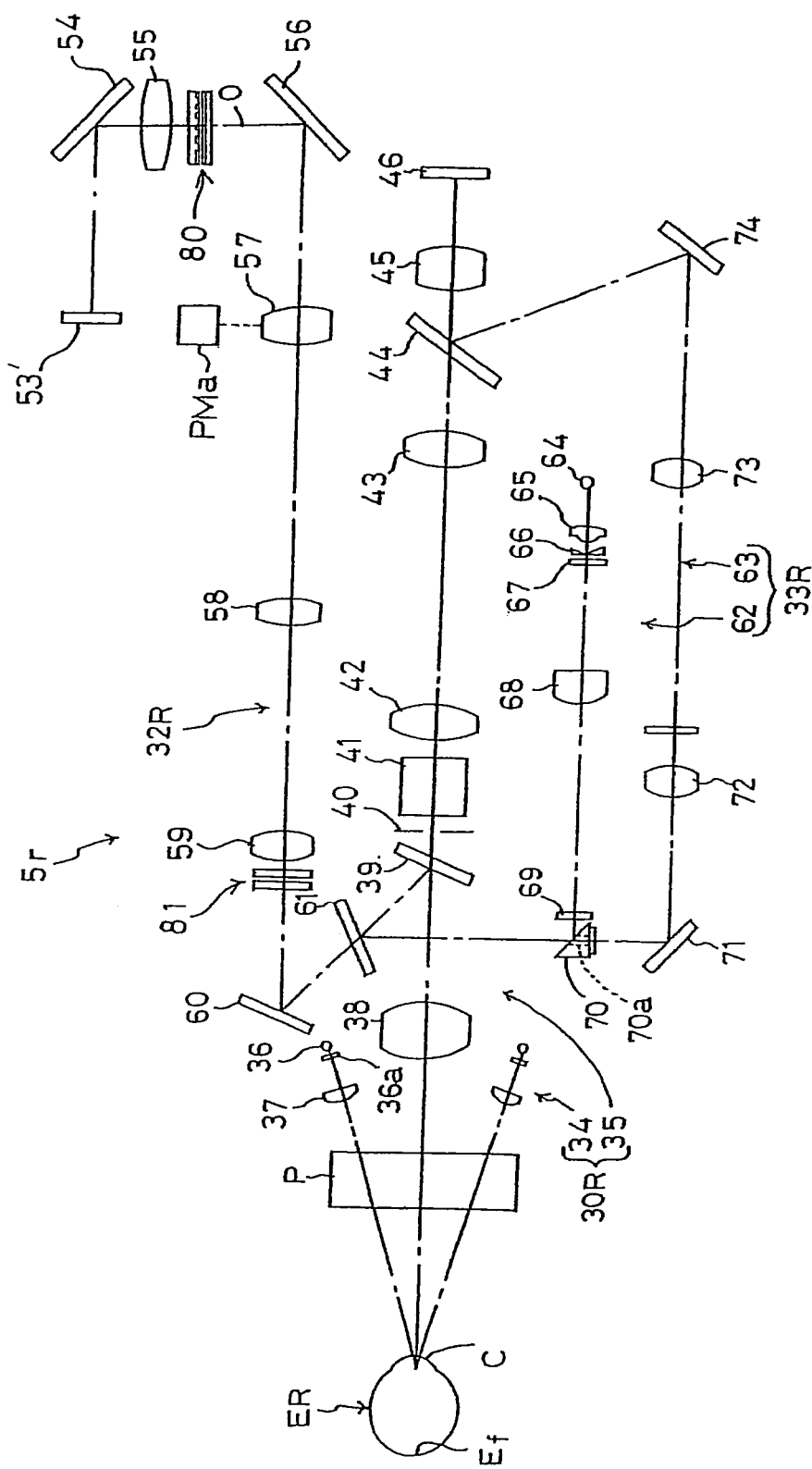
FIG. 25 is an explanatory view showing an example in which a liquid crystal display is used instead of the rotational target plate in the optical system in FIG. 7.
Figure 26A:
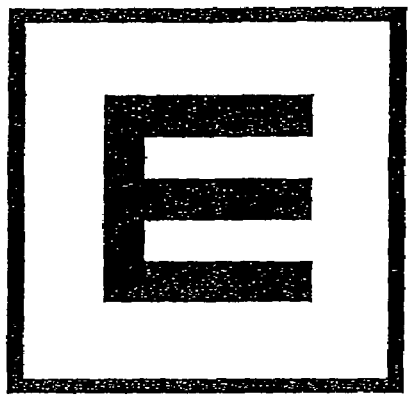
FIG. 26(a) is an explanatory view showing an example in which a rectangular fusion frame is combined with a so called E character target.
Figure 26B:
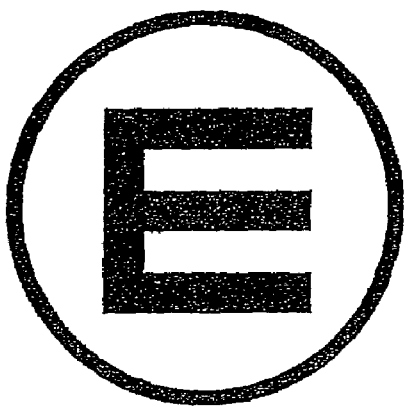
FIG. 26(b) is an explanatory view showing an example in which a circular fusion frame is combined with an E character target.
Figure 26C:
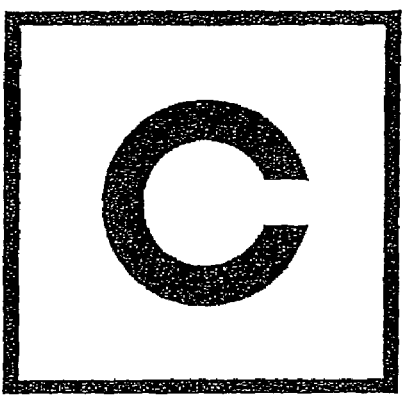
FIG. 26(c) is an explanatory view showing an example in which the rectangular fusion frame is combined with the target of the Landolt ring.
Figure 26D:
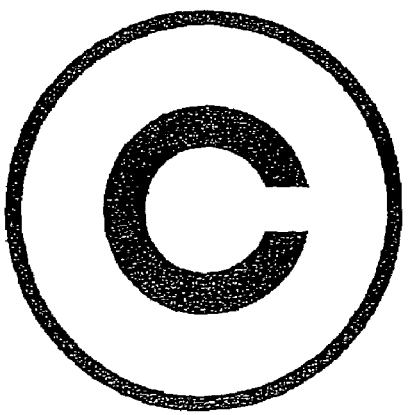
FIG. 26(d) is an explanatory view showing an example in which the circular fusion frame is combined with the target of the Landolt ring.

However, for example, if the target is projected by use of a liquid crystal display 53' a shown in FIGS. 24 and 25 instead of the rotational target plate 53, for example, it is possible to further miniaturize and simplify the apparatus that the fusion frame is projected on the liquid crystal display 53' and the LED 91, it is preferable that the collimator lens 92, the fusion frame chart 93 and the reflective mirror 94 are removed.

Furthermore, in the optometric apparatus 2, when the Landolt ring is changed, because the rotational target plate 53 is rotated rightward and leftward as viewed from the examinee 4, if the fusion frame chart is provided in the target chart of the rotational target plate 53 as shown in FIG. 5, the fusion operation for the examinee 4 is not lost in comparison with the case in which the fusion frame 95 is deviated upward and downward even though the fusion frame 95 deviates rightward and leftward by a stop position of the rotational target plate being deviated in one of the body portions 5l and 5r.

Meanwhile, the present invention is not limited to the aforementioned embodiments, for example, various changes with respect to a combination of a shape of the target and a shape of the fusion frame may be made as shown in FIG. 26. Moreover, the fusion pattern is not limited to a frame shape as the fusion frame, necessarily, for example, it may be a form arranging points in a frame shape and surrounding the target, but, it is possible to accomplish more effectively the fusion operation in the frame-shaped fusion pattern as described above, because the examinee is difficult to know, in comparison two point-shaped same patterns (two patterns projected by the body portions 5l and 5r) with two line-shaped same patterns, even if the patterns are deviated (even if the fusion is not achieved).

INDUSTRIAL APPLICABILITY

The present invention makes it possible to prevent the projection chart of the optical system for the right eye and the projection chart of the optical system for the left eye from seeing in a deviated condition, it is possible to apply widely the present invention to an apparatus for performing an inspection of the both eyes.

The invention claimed is:

1. An optometric apparatus, comprising:
an optical system for a right eye, for projecting a chart for the right eye; and
an optical system for a left eye, for projecting a chart for the left eye, in order to inspect visual function of both eyes of an examinee, wherein
said optical systems for the right and left eyes project the same fusion patterns in order to perform a fusion of both eyes of the examinee,
said optical systems for the right and left eyes project targets for inspecting visions as the charts for the right and left eyes, and
a distance from eyes of the examinee to be examined to the targets for inspecting the visions is variable optically and a convergence angle determined by optical axes of the optical systems for the right and left eyes varies pursuant to said distance.

2. The optometric apparatus according to claim 1, wherein the optical system for the right eye comprises means for projecting the chart for the right eye, and means for projecting the fusion pattern for the right eye, and the optical system for the left eye comprises means for projecting the chart for the left eye and means for projecting the fusion pattern for the left eye, and wherein said means for projecting the fusion pattern for the right eye is provided separately from said means for projecting the chart for the right eye, and said means for projecting the fusion pattern for the left eye is provided separately from the means for projecting the chart for the left eye.

3. An optometric apparatus, comprising:
an optical system for a right eye, for projecting a chart for the right eye; and
an optical system for a left eye, for projecting a chart for the left eye, in order to inspect visual function of both eyes of an examinee, wherein
said optical systems for the right and left eyes project the same fusion patterns in order to perform a fusion of both eyes of the examinee,
said fusion pattern is formed into a frame shape to surround the charts for the right and left eyes when the fusion pattern is projected simultaneously with the charts for the right and left eyes,
said optical systems for the right and left eyes project targets for inspecting visions as the charts for the right and left eyes, and
a distance from eyes of the examinee to be examined to the targets for inspecting the visions is variable optically and a convergence angle determined by optical axes of the optical systems for the right and left eyes varies pursuant to said distance.

4. An optometric apparatus, comprising:
an optical system for a right eye, for projecting a chart for the right eye; and
an optical system for a left eye, for projecting a chart for the left eye, in order to inspect visual function of both eyes of an examinee, wherein
said optical systems for the right and left eyes project the same fusion patterns in order to perform a fusion of both eyes of the examinee,
said fusion pattern is projected by either of two colors being colored selectively,
said optical systems for the right and left eyes project targets for inspecting visions as the charts for the right and left eyes, and
a distance from eyes of the examinee to be examined to the targets for inspecting the visions is variable optically and a convergence angle determined by optical axes of the optical systems for the right and left eyes varies pursuant to said distance.

5. An optometric apparatus, comprising:
an optical system for a right eye, for projecting a chart for the right eye; and
an optical system for a left eye, for projecting a chart for the left eye, in order to inspect visual function of both eyes of an examinee, wherein
said optical systems for the right and left eyes project the same fusion patterns in order to perform a fusion of both eyes of the examinee,
said optical systems for the right and left eyes project targets for inspecting oblique positions as the charts for the right and left eyes,
said optical systems for the right and left eyes project targets for inspecting visions as the charts for the right and left eyes, and
a distance from eyes of the examinee to be examined to the targets for inspecting the visions is variable optically and a convergence angle determined by optical axes, of the optical systems for the right and left eyes varies pursuant to said distance.

6. An optometric apparatus, comprising:
an optical system for a right eye, for projecting a chart for the right eye; and
an optical system for a left eye, for projecting a chart for the left eye, in order to inspect visual function of both eyes of an examinee, wherein
said optical systems for the right and left eyes project the same fusion patterns in order to perform a fusion of both eyes of the examinee, and
the optical system for the right eye comprises means for projecting the chart for the right eye, and means for projecting the fusion pattern for the right eye, and the optical system for the left eye comprises means for projecting the chart for the left eye and means for projecting the fusion pattern for the left eye, and wherein said means for projecting the fusion pattern for the right eye is provided separately from said means for projecting the chart for the right eye, and said means for projecting the fusion pattern for the left eye is provided separately from the means for projecting the chart for the left eye.

7. An optometric apparatus, comprising:
an optical system for a right eye, for projecting a chart for the right eye; and
an optical system for a left eye, for projecting a chart for the left eye, in order to inspect visual function of both eyes of an examinee, wherein
said optical systems for the right and left eyes project the same fusion patterns in order to perform a fusion of both eyes of the examinee,
said fusion pattern is formed into a frame shape to surround the charts for the right and left eyes when the fusion pattern is projected simultaneously with the charts for the right and left eyes, and
the optical system for the right eye comprises means for projecting the chart for the right eye, and means for projecting the fusion pattern for the right eye, and the optical system for the left eye comprises means for projecting the chart for the left eye and means for projecting the fusion pattern for the left eye, and wherein said means for projecting the fusion pattern for the right eye is provided separately from said means for projecting the chart for the right eye, and said means for projecting the fusion pattern for the left eye is provided separately from the means for projecting the chart for the left eye.

8. An optometric apparatus, comprising:
an optical system for a right eye, for projecting a chart for the right eye; and
an optical system for a left eye, for projecting a chart for the left eye, in order to inspect visual function of both eyes of an examinee, wherein
said optical systems for the right and left eyes project the same fusion patterns in order to perform a fusion of both eyes of the examinee,
said fusion pattern is projected by either of two colors being colored selectively, and
the optical system for the right eye comprises means for projecting the chart for the right eye, and means for projecting the fusion pattern for the right eye, and the optical system for the left eye comprises means for projecting the chart for the left eye and means for projecting the fusion pattern for the left eye, and wherein said means for projecting the fusion pattern for the right eye is provided separately from said means for projecting the chart for the right eye, and said means for projecting the fusion pattern for the left eye is provided separately from the means for projecting the chart for the left eye.

9. An optometric apparatus, comprising:
an optical system for a right eye, for projecting a chart for the right eye; and
an optical system for a left eye, for projecting a chart for the left eye, in order to inspect visual function of both eyes of an examinee, wherein
said optical systems for the right and left eyes project the same fusion patterns in order to perform a fusion of both eyes of the examinee,
said optical systems for the right and left eyes project targets for inspecting oblique positions as the charts for the right and left eyes, and
the optical system for the right eye comprises means for projecting the chart for the right eye, and means for projecting the fusion pattern for the right eye, and the optical system for the left eye comprises means for projecting the chart for the left eye and means for projecting the fusion pattern for the left eye, and wherein said means for projecting the fusion pattern for the right eye is provided separately from said means for projecting the chart for the right eye, and said means for projecting the fusion pattern for the left eye is provided separately from the means for projecting the chart for the left eye.

10. An optometric apparatus, comprising:
an optical system for a right eye, for projecting a chart for the right eye; and
an optical system for a left eye, for projecting a chart for the left eye, in order to inspect visual function of both eyes of an examinee, wherein
said optical systems for the right and left eyes project the same fusion patterns in order to perform a fusion of both eyes of the examinee,
said optical systems for the right and left eyes project targets for inspecting visions as the charts for the right and left eyes, and
the optical system for the right eye comprises means for projecting the chart for the right eye, and means for projecting the fusion pattern for the right eye, and the optical system for the left eye comprises means for projecting the chart for the left eye and means for projecting the fusion pattern for the left eye, and wherein said means for projecting the fusion pattern for the right eye is provided separately from said means for projecting the chart for the right eye, and said means for projecting the fusion pattern for the left eye is provided separately from the means for projecting the chart for the left eye.

* * * * *